(12) United States Patent
Penagondla et al.

(10) Patent No.: US 11,771,819 B2
(45) Date of Patent: Oct. 3, 2023

(54) LOW PROFILE FILTER DEVICES SUITABLE FOR USE IN NEGATIVE PRESSURE WOUND THERAPY SYSTEMS

(71) Applicant: ConvaTec Limited, Flintshire (GB)

(72) Inventors: Manjunath Penagondla, Warrington (GB); Colin Wood, Flintshire (GB)

(73) Assignee: ConvaTec Limited, Flintshire (GB)

( * ) Notice: Subject to any disclaimer, the term of this patent is extended or adjusted under 35 U.S.C. 154(b) by 660 days.

(21) Appl. No.: 16/728,417

(22) Filed: Dec. 27, 2019

(65) Prior Publication Data

US 2021/0196867 A1 Jul. 1, 2021

(51) Int. Cl.
*A61M 1/00* (2006.01)
*A61M 39/10* (2006.01)
*A61F 13/00* (2006.01)

(52) U.S. Cl.
CPC .............. *A61M 1/882* (2021.05); *A61M 1/90* (2021.05); *A61M 39/10* (2013.01); *A61F 13/00068* (2013.01); *A61M 2039/1077* (2013.01); *A61M 2039/1083* (2013.01); *A61M 2039/1088* (2013.01); *A61M 2202/0028* (2013.01); *A61M 2205/584* (2013.01);
(Continued)

(58) Field of Classification Search
CPC ........ A61M 1/882; A61M 1/90; A61M 39/10; A61M 2039/1077; A61M 2039/1083; A61M 2039/1088; A61M 2202/0028; A61M 2205/584; A61M 2205/6036; A61M 2205/7536; A61M 2205/7563; A61M 2206/12; A61M 1/784; A61M 1/86; A61M 1/913; A61M 1/982; A61M 1/73; A61M 2205/7527; A61M 2039/1027; A61M 2039/1061; A61F 13/00068
See application file for complete search history.

(56) References Cited

U.S. PATENT DOCUMENTS 2,881,771 A    4/1959 Touey
4,166,792 A *  9/1979 Offer .................... B01D 35/147
                                                210/446
(Continued)

FOREIGN PATENT DOCUMENTS

CN    204812020 U    12/2015
EP      1270202 A2    1/2003
(Continued)

*Primary Examiner* — Susan S Su
*Assistant Examiner* — Eric Rassavong
(74) *Attorney, Agent, or Firm* — Taft Stettinius & Hollister LLP; Ryan O. White; Derek B. Lavender

(57) ABSTRACT

A filter adaptor includes a body that defines an internal passageway disposed between an inlet and an outlet, the passageway configured to permit passage of a fluid in a first direction defined by the inlet and the outlet; and a filter disposed within the passageway and oriented to define a volumetric direction that is different than the first direction. Another filter adaptor includes a body that defines an internal passageway disposed between an inlet and an outlet, and a filter disposed within the passageway, wherein the filter comprises a gelling absorbent material that, when in a dry state, is permeable to gas and that, when contacted by an aqueous fluid, converts to a gel. Such filter adaptors may be used for negative pressure wound therapy, dressing, or as syringe filters.

15 Claims, 12 Drawing Sheets

(52) U.S. Cl.
CPC .............. *A61M 2205/6036* (2013.01); *A61M 2205/7536* (2013.01); *A61M 2205/7563* (2013.01); *A61M 2206/12* (2013.01)

(56) References Cited

U.S. PATENT DOCUMENTS

| | | | |
|---|---|---|---|
| 4,505,822 A * | 3/1985 | Blomback | B01D 71/74 |
| | | | 435/239 |
| 4,721,563 A | 1/1988 | Rosaen | |
| 5,711,884 A * | 1/1998 | Asher | G02B 5/203 |
| | | | 210/639 |
| 6,423,215 B1 | 7/2002 | Stein | |
| 10,016,537 B2 | 7/2018 | Menon et al. | |
| 10,046,096 B2 | 8/2018 | Askem et al. | |
| 10,076,447 B2 | 9/2018 | Barta et al. | |
| 10,076,587 B2 | 9/2018 | Locke et al. | |
| 10,143,784 B2 | 12/2018 | Walton et al. | |
| 10,426,670 B2 | 10/2019 | vom Blucher et al. | |
| 10,426,747 B2 | 10/2019 | Johnson | |
| 10,426,874 B2 | 10/2019 | Chien et al. | |
| 10,426,875 B2 | 10/2019 | Blott et al. | |
| 10,426,938 B2 | 10/2019 | Locke et al. | |
| 10,434,015 B2 | 10/2019 | Taylor et al. | |
| 10,434,142 B2 | 10/2019 | Niazi et al. | |
| 10,434,210 B2 | 10/2019 | Olson et al. | |
| 10,434,284 B2 | 10/2019 | Hanson et al. | |
| 10,449,094 B2 | 10/2019 | Donda et al. | |
| D866,756 S | 11/2019 | Allen et al. | |
| 10,463,760 B2 | 11/2019 | Karthikeyan et al. | |
| 10,463,773 B2 | 11/2019 | Haggstrom et al. | |
| 10,470,933 B2 | 11/2019 | Riesinger | |
| 10,470,936 B2 | 11/2019 | Wohlgemuth et al. | |
| 10,471,122 B2 | 11/2019 | Shi et al. | |
| 10,471,190 B2 | 11/2019 | Locke et al. | |
| 10,478,345 B2 | 11/2019 | Barta et al. | |
| 10,478,346 B2 | 11/2019 | Knutson | |
| 10,478,394 B2 | 11/2019 | Yu | |
| 10,485,707 B2 | 11/2019 | Sexton | |
| 10,485,891 B2 | 11/2019 | Andrews et al. | |
| 10,485,892 B2 | 11/2019 | Hands et al. | |
| 10,485,906 B2 | 11/2019 | Freedman et al. | |
| 10,486,135 B2 | 11/2019 | Yang et al. | |
| 10,492,956 B2 | 12/2019 | Zamierowski | |
| 10,493,178 B2 | 12/2019 | Marchant et al. | |
| 10,493,184 B2 | 12/2019 | Collinson et al. | |
| 10,493,185 B2 | 12/2019 | Stokes et al. | |
| 10,500,099 B2 | 12/2019 | Hung et al. | |
| 10,500,103 B2 | 12/2019 | Croizat et al. | |
| 10,500,104 B2 | 12/2019 | Sookraj | |
| 10,500,173 B2 | 12/2019 | Yang et al. | |
| 10,500,235 B2 | 12/2019 | Wardell | |
| 10,500,300 B2 | 12/2019 | Dybe et al. | |
| 10,500,301 B2 | 12/2019 | Laurensou | |
| 10,500,302 B2 | 12/2019 | Holm et al. | |
| 10,501,487 B2 | 12/2019 | Andrews et al. | |
| 10,506,928 B2 | 12/2019 | Locke et al. | |
| 10,507,141 B2 | 12/2019 | Allen et al. | |
| 10,507,259 B2 | 12/2019 | Cree et al. | |
| 10,512,707 B2 | 12/2019 | Whalen, III et al. | |
| 10,525,170 B2 | 1/2020 | Havenstrite et al. | |
| 10,532,137 B2 | 1/2020 | Pratt et al. | |
| 10,532,194 B2 | 1/2020 | Locke et al. | |
| 10,537,657 B2 | 1/2020 | Phillips et al. | |
| 10,542,936 B2 | 1/2020 | Goldberg et al. | |
| 10,543,133 B2 | 1/2020 | Shaw et al. | |
| 10,543,293 B2 | 1/2020 | Suschek | |
| 10,548,777 B2 | 2/2020 | Locke et al. | |
| 10,549,008 B2 | 2/2020 | Yoo | |
| 10,549,016 B2 | 2/2020 | Bushko et al. | |
| 10,549,017 B2 | 2/2020 | Hsiao et al. | |
| 10,555,838 B2 | 2/2020 | Wu et al. | |
| 10,555,839 B2 | 2/2020 | Hartwell | |
| 10,556,044 B2 | 2/2020 | Robinson et al. | |
| 10,561,533 B2 | 2/2020 | Hoggarth et al. | |
| 10,561,536 B2 | 2/2020 | Holm et al. | |
| 10,568,767 B2 | 2/2020 | Addison et al. | |
| 10,568,768 B2 | 2/2020 | Long et al. | |
| 10,568,770 B2 | 2/2020 | Robinson et al. | |
| 10,568,771 B2 | 2/2020 | MacDonald et al. | |
| 10,568,773 B2 | 2/2020 | Tuck et al. | |
| 10,568,983 B2 | 2/2020 | Gerdes et al. | |
| 10,575,991 B2 | 3/2020 | Dunn | |
| 10,575,992 B2 | 3/2020 | Sarangapani et al. | |
| 10,576,037 B2 | 3/2020 | Harrell | |
| 10,576,189 B2 | 3/2020 | Locke et al. | |
| 10,583,042 B2 | 3/2020 | Sarangapani et al. | |
| 10,583,228 B2 | 3/2020 | Shuler et al. | |
| 10,589,007 B2 | 3/2020 | Coulthard et al. | |
| 10,590,184 B2 | 3/2020 | Kuo | |
| 10,610,414 B2 | 4/2020 | Hartwell et al. | |
| 10,610,415 B2 | 4/2020 | Griffey et al. | |
| 10,610,623 B2 | 4/2020 | Robinson et al. | |
| 10,617,569 B2 | 4/2020 | Bonn | |
| 10,617,608 B2 | 4/2020 | Shin et al. | |
| 10,617,769 B2 | 4/2020 | Huang | |
| 10,617,784 B2 | 4/2020 | Yu et al. | |
| 10,617,786 B2 | 4/2020 | Kluge et al. | |
| 10,618,266 B2 | 4/2020 | Wright et al. | |
| 10,624,984 B2 | 4/2020 | Courage et al. | |
| 10,625,002 B2 | 4/2020 | Locke et al. | |
| 10,632,019 B2 | 4/2020 | Vitaris | |
| 10,632,224 B2 | 4/2020 | Hardy et al. | |
| 10,639,206 B2 | 5/2020 | Hu et al. | |
| 10,639,350 B2 | 5/2020 | Arber et al. | |
| 10,639,404 B2 | 5/2020 | Lichtenstein | |
| 10,646,614 B2 | 5/2020 | Grinstaff et al. | |
| 10,653,562 B2 | 5/2020 | Robinson et al. | |
| 10,653,782 B2 | 5/2020 | Ameer et al. | |
| 10,653,810 B2 | 5/2020 | Datt et al. | |
| 10,653,821 B2 | 5/2020 | Nichols | |
| 10,653,823 B2 | 5/2020 | Bharti et al. | |
| 10,660,799 B2 | 5/2020 | Wu et al. | |
| 10,660,851 B2 | 5/2020 | Millis et al. | |
| 10,660,992 B2 | 5/2020 | Canner et al. | |
| 10,660,994 B2 | 5/2020 | Askem et al. | |
| 10,667,955 B2 | 6/2020 | Allen et al. | |
| 10,667,956 B2 | 6/2020 | Van Holten et al. | |
| 10,682,257 B2 | 6/2020 | Lu | |
| 10,682,258 B2 | 6/2020 | Manwaring et al. | |
| 10,682,259 B2 | 6/2020 | Hunt et al. | |
| 10,682,318 B2 | 6/2020 | Twomey et al. | |
| 10,682,386 B2 | 6/2020 | Ellis-Behnke et al. | |
| 10,682,446 B2 | 6/2020 | Askem et al. | |
| 10,687,983 B2 | 6/2020 | Dahlberg et al. | |
| 10,687,985 B2 | 6/2020 | Lee et al. | |
| 10,688,215 B2 | 6/2020 | Munro et al. | |
| 10,688,217 B2 | 6/2020 | Hanson et al. | |
| RE48,117 E | 7/2020 | Albert et al. | |
| 10,702,419 B2 | 7/2020 | Locke et al. | |
| 10,702,420 B2 | 7/2020 | Hammond et al. | |
| 10,703,942 B2 | 7/2020 | Tunius | |
| 10,709,760 B2 | 7/2020 | Gronberg et al. | |
| 10,709,807 B2 | 7/2020 | Kshirsagar | |
| 10,709,883 B2 | 7/2020 | Spector | |
| 10,716,711 B2 | 7/2020 | Locke et al. | |
| 10,716,874 B2 | 7/2020 | Koyama et al. | |
| 10,729,589 B2 | 8/2020 | Dorian et al. | |
| 10,729,590 B2 | 8/2020 | Simmons et al. | |
| 10,729,826 B2 | 8/2020 | Lin | |
| 10,736,787 B2 | 8/2020 | Hannigan et al. | |
| 10,736,788 B2 | 8/2020 | Locke et al. | |
| 10,736,985 B2 | 8/2020 | Odermatt et al. | |
| 10,737,003 B2 | 8/2020 | Fujisaki | |
| 10,743,900 B2 | 8/2020 | Ingram et al. | |
| 10,744,040 B2 | 8/2020 | Kazala, Jr. et al. | |
| 10,744,041 B2 | 8/2020 | Hartwell | |
| 10,744,225 B2 | 8/2020 | Lindgren et al. | |
| 10,744,237 B2 | 8/2020 | Guidi et al. | |
| 10,744,238 B2 | 8/2020 | Guidi et al. | |
| 10,744,239 B2 | 8/2020 | Armstrong et al. | |
| 10,744,240 B2 | 8/2020 | Simmons et al. | |
| 10,751,212 B2 | 8/2020 | Raza et al. | |
| 10,751,442 B2 | 8/2020 | Bonnefin et al. | |
| 10,751,452 B2 | 8/2020 | Topaz | |

(56) References Cited

U.S. PATENT DOCUMENTS

| | | |
|---|---|---|
| 10,758,423 B2 | 9/2020 | Pigg et al. |
| 10,758,424 B2 | 9/2020 | Blott et al. |
| 10,758,425 B2 | 9/2020 | Blott et al. |
| 10,758,426 B2 | 9/2020 | Eddy |
| 10,758,651 B2 | 9/2020 | Blott et al. |
| 10,765,561 B2 | 9/2020 | Lattimore et al. |
| 10,765,783 B2 | 9/2020 | Locke et al. |
| 10,772,767 B2 | 9/2020 | Bjork et al. |
| 10,772,999 B2 | 9/2020 | Svensby |
| 10,779,993 B2 | 9/2020 | Bishop et al. |
| 10,780,114 B2 | 9/2020 | Udagawa et al. |
| 10,780,194 B2 | 9/2020 | Flach et al. |
| 10,780,201 B2 | 9/2020 | Lin |
| 10,780,202 B2 | 9/2020 | Askem et al. |
| 10,780,203 B2 | 9/2020 | Coulthard et al. |
| 10,782,238 B2 | 9/2020 | Hicks et al. |
| 10,792,191 B2 | 10/2020 | Robinson et al. |
| 10,792,192 B2 | 10/2020 | Tout et al. |
| 10,792,337 B2 | 10/2020 | Leung et al. |
| 10,792,404 B2 | 10/2020 | Hu et al. |
| 10,792,482 B2 | 10/2020 | Randolph et al. |
| 10,800,905 B2 | 10/2020 | Delli-Santi et al. |
| 10,806,819 B2 | 10/2020 | Shuler |
| 11,026,844 B2 | 6/2021 | Locke et al. |
| 11,058,588 B2 | 7/2021 | Albert et al. |
| 11,154,650 B2 | 10/2021 | Robinson et al. |
| 11,207,442 B2 | 12/2021 | Locke et al. |
| 2002/0126187 A1 | 9/2002 | Ison et al. |
| 2006/0021624 A1 | 2/2006 | Gonterman et al. |
| 2006/0155260 A1 | 7/2006 | Blott et al. |
| 2006/0172000 A1 | 8/2006 | Cullen et al. |
| 2007/0185426 A1 | 8/2007 | Ambrosio et al. |
| 2007/0219512 A1 | 9/2007 | Heaton et al. |
| 2007/0239078 A1 | 10/2007 | Jaeb |
| 2009/0227969 A1* | 9/2009 | Jaeb ............... A61M 1/962 604/313 |
| 2009/0234307 A1 | 9/2009 | Vitaris |
| 2009/0259203 A1 | 10/2009 | Hu et al. |
| 2009/0293887 A1 | 12/2009 | Wilkes et al. |
| 2009/0299303 A1 | 12/2009 | Seegert |
| 2010/0015208 A1 | 1/2010 | Kershaw et al. |
| 2010/0030178 A1 | 2/2010 | MacMeccan et al. |
| 2010/0125233 A1 | 5/2010 | Edward S. et al. |
| 2010/0125258 A1 | 5/2010 | Coulthard et al. |
| 2010/0137775 A1 | 6/2010 | Hu et al. |
| 2010/0185163 A1 | 7/2010 | Heagle |
| 2010/0298790 A1 | 11/2010 | Guidi et al. |
| 2011/0015595 A1 | 1/2011 | Robinson et al. |
| 2011/0028918 A1 | 2/2011 | Hartwell |
| 2011/0112457 A1 | 5/2011 | Holm et al. |
| 2011/0178451 A1 | 7/2011 | Robinson et al. |
| 2011/0224593 A1 | 9/2011 | Tunius |
| 2011/0224630 A1 | 9/2011 | Simmons et al. |
| 2011/0230849 A1 | 9/2011 | Coulthard et al. |
| 2011/0251566 A1 | 10/2011 | Zimnitsky et al. |
| 2011/0257572 A1 | 10/2011 | Locke et al. |
| 2011/0257573 A1 | 10/2011 | Hong et al. |
| 2011/0275972 A1 | 11/2011 | Rosenberg |
| 2012/0071845 A1 | 3/2012 | Hu et al. |
| 2012/0130332 A1 | 5/2012 | Cotton et al. |
| 2012/0136325 A1 | 5/2012 | Allen et al. |
| 2012/0209226 A1 | 8/2012 | Simmons et al. |
| 2013/0053795 A1 | 2/2013 | Coulthard et al. |
| 2013/0092636 A1* | 4/2013 | Festner ............... B01D 27/142 210/346 |
| 2013/0123728 A1 | 5/2013 | Pratt et al. |
| 2013/0226063 A1 | 8/2013 | Taylor et al. |
| 2014/0005618 A1 | 1/2014 | Locke et al. |
| 2014/0074053 A1* | 3/2014 | Locke ............... A61M 1/90 156/60 |
| 2014/0188060 A1 | 7/2014 | Robinson et al. |
| 2014/0194838 A1 | 7/2014 | Wibaux et al. |
| 2014/0200532 A1 | 7/2014 | Robinson et al. |
| 2014/0236112 A1 | 8/2014 | Von Wolff et al. |
| 2014/0256925 A1 | 9/2014 | Catchmark et al. |
| 2014/0276499 A1 | 9/2014 | Locke et al. |
| 2014/0296804 A1 | 10/2014 | Hicks et al. |
| 2014/0308338 A1 | 10/2014 | Nierle et al. |
| 2014/0309574 A1 | 10/2014 | Cotton |
| 2015/0018433 A1 | 1/2015 | Leipzig et al. |
| 2015/0057624 A1 | 2/2015 | Simmons et al. |
| 2015/0071985 A1 | 3/2015 | Walker et al. |
| 2015/0079152 A1 | 3/2015 | Wuollett et al. |
| 2015/0094674 A1 | 4/2015 | Pratt et al. |
| 2015/0104486 A1 | 4/2015 | Bonnefin et al. |
| 2015/0112311 A1 | 4/2015 | Hammond et al. |
| 2015/0119831 A1 | 4/2015 | Robinson et al. |
| 2015/0119834 A1 | 4/2015 | Locke et al. |
| 2015/0141941 A1 | 5/2015 | Allen et al. |
| 2015/0148785 A1 | 5/2015 | Kleiner |
| 2015/0174304 A1 | 6/2015 | Askem et al. |
| 2015/0245949 A1 | 9/2015 | Locke et al. |
| 2015/0246164 A1 | 9/2015 | Heaton et al. |
| 2015/0250979 A1 | 9/2015 | Loske |
| 2015/0265741 A1 | 9/2015 | Duncan et al. |
| 2015/0265743 A1 | 9/2015 | Hanson et al. |
| 2015/0320901 A1 | 11/2015 | Chandrashekhar-Bhat et al. |
| 2016/0008293 A1 | 1/2016 | Shi et al. |
| 2016/0038626 A1 | 2/2016 | Locke et al. |
| 2016/0051724 A1 | 2/2016 | Sahin et al. |
| 2016/0067107 A1 | 3/2016 | Cotton |
| 2016/0100987 A1 | 4/2016 | Hartwell et al. |
| 2016/0106878 A1 | 4/2016 | Yang et al. |
| 2016/0106892 A1 | 4/2016 | Hartwell |
| 2016/0166422 A1 | 6/2016 | Karim et al. |
| 2016/0193244 A1 | 7/2016 | Ota et al. |
| 2016/0222548 A1 | 8/2016 | Agboh |
| 2016/0271178 A1 | 9/2016 | Hauser et al. |
| 2016/0287743 A1 | 10/2016 | Andrews |
| 2016/0339158 A1 | 11/2016 | Collinson et al. |
| 2016/0374847 A1 | 12/2016 | Lachenbruch et al. |
| 2017/0014275 A1 | 1/2017 | Schneider |
| 2017/0049111 A1 | 2/2017 | Patton et al. |
| 2017/0072669 A1 | 3/2017 | Sekido et al. |
| 2017/0128269 A1 | 5/2017 | Coulthard et al. |
| 2017/0189237 A1 | 7/2017 | Locke et al. |
| 2017/0189575 A1 | 7/2017 | Lee et al. |
| 2017/0209615 A1 | 7/2017 | Tornero Garcia et al. |
| 2017/0232161 A1 | 8/2017 | Fewkes et al. |
| 2017/0258956 A1 | 9/2017 | Flach et al. |
| 2017/0367895 A1 | 12/2017 | Holm et al. |
| 2017/0368239 A1 | 12/2017 | Askem et al. |
| 2018/0008742 A1 | 1/2018 | Hoggarth et al. |
| 2018/0014974 A1 | 1/2018 | Hoggarth et al. |
| 2018/0023217 A1 | 1/2018 | Patton et al. |
| 2018/0030321 A1 | 2/2018 | Tunius |
| 2018/0042789 A1 | 2/2018 | Bradford et al. |
| 2018/0078423 A1 | 3/2018 | Magin et al. |
| 2018/0086903 A1 | 3/2018 | Zhang et al. |
| 2018/0118809 A1 | 5/2018 | Mearns Spragg |
| 2018/0133066 A1 | 5/2018 | Ahsani et al. |
| 2018/0140467 A1 | 5/2018 | Hunt |
| 2018/0140822 A1 | 5/2018 | Robinson et al. |
| 2018/0200414 A1 | 7/2018 | Askem et al. |
| 2018/0221531 A1 | 8/2018 | Bender et al. |
| 2018/0236124 A1 | 8/2018 | Young et al. |
| 2018/0243463 A1 | 8/2018 | Chatterjee et al. |
| 2018/0243464 A1 | 8/2018 | Hwang et al. |
| 2018/0244857 A1 | 8/2018 | Lee et al. |
| 2018/0256878 A1* | 9/2018 | Ciccone ............... F16L 37/36 |
| 2018/0272052 A1 | 9/2018 | Locke et al. |
| 2018/0296397 A1 | 10/2018 | Askem et al. |
| 2018/0303873 A1 | 10/2018 | Been et al. |
| 2018/0311419 A1 | 11/2018 | Locke et al. |
| 2018/0333522 A1 | 11/2018 | Pratt et al. |
| 2018/0344533 A1 | 12/2018 | Rovaniemi |
| 2018/0353334 A1 | 12/2018 | Locke et al. |
| 2018/0353337 A1 | 12/2018 | Locke |
| 2018/0353339 A1 | 12/2018 | Locke et al. |
| 2018/0353340 A1 | 12/2018 | Robinson et al. |
| 2018/0353344 A1 | 12/2018 | Locke et al. |
| 2018/0353662 A1 | 12/2018 | Locke et al. |
| 2018/0353663 A1 | 12/2018 | Locke et al. |
| 2018/0360667 A1 | 12/2018 | Droche |

(56) References Cited

U.S. PATENT DOCUMENTS

| | | |
|---|---|---|
| 2019/0000677 A1 | 1/2019 | Munro |
| 2019/0015258 A1 | 1/2019 | Gowans et al. |
| 2019/0015468 A1 | 1/2019 | Yadav et al. |
| 2019/0030223 A1 | 1/2019 | Lin |
| 2019/0046682 A1 | 2/2019 | Choi et al. |
| 2019/0060127 A1 | 2/2019 | Locke et al. |
| 2019/0083752 A1 | 3/2019 | Howell et al. |
| 2019/0117465 A1 | 4/2019 | Osborne et al. |
| 2019/0117466 A1 | 4/2019 | Kazala, Jr. et al. |
| 2019/0117861 A1 | 4/2019 | Locke et al. |
| 2019/0125590 A1 | 5/2019 | Rehbein et al. |
| 2019/0133830 A1 | 5/2019 | Bishop et al. |
| 2019/0151155 A1 | 5/2019 | Bonn |
| 2019/0151159 A1 | 5/2019 | Gowans et al. |
| 2019/0151495 A1 | 5/2019 | Helary et al. |
| 2019/0184052 A1 | 6/2019 | Ilan et al. |
| 2019/0231600 A1 | 8/2019 | Locke et al. |
| 2019/0231602 A1 | 8/2019 | Locke et al. |
| 2019/0231943 A1 | 8/2019 | Robinson et al. |
| 2019/0274889 A1 | 9/2019 | Steward et al. |
| 2019/0282728 A1 | 9/2019 | Kellar et al. |
| 2019/0290799 A1 | 9/2019 | Arshi et al. |
| 2019/0298249 A1 | 10/2019 | Bates et al. |
| 2019/0298577 A1 | 10/2019 | Locke et al. |
| 2019/0298578 A1 | 10/2019 | Shulman et al. |
| 2019/0298579 A1 | 10/2019 | Moore et al. |
| 2019/0298580 A1 | 10/2019 | Hall et al. |
| 2019/0298582 A1 | 10/2019 | Addison et al. |
| 2019/0298881 A1 | 10/2019 | Ramjit et al. |
| 2019/0298882 A1 | 10/2019 | Nelson |
| 2019/0298895 A1 | 10/2019 | Selby et al. |
| 2019/0307611 A1 | 10/2019 | Askem et al. |
| 2019/0307612 A1 | 10/2019 | Hartwell et al. |
| 2019/0307934 A1 | 10/2019 | Allen et al. |
| 2019/0307935 A1 | 10/2019 | Simmons et al. |
| 2019/0314187 A1 | 10/2019 | Emslander et al. |
| 2019/0314209 A1 | 10/2019 | Ha et al. |
| 2019/0314544 A1 | 10/2019 | Filho et al. |
| 2019/0321232 A1 | 10/2019 | Jardret et al. |
| 2019/0321509 A1 | 10/2019 | Chakravarthy et al. |
| 2019/0321526 A1 | 10/2019 | Robinson et al. |
| 2019/0322795 A1 | 10/2019 | Kubo et al. |
| 2019/0328580 A1 | 10/2019 | Emslander et al. |
| 2019/0336343 A1 | 11/2019 | Etchells et al. |
| 2019/0336344 A1 | 11/2019 | Locke |
| 2019/0336345 A1 | 11/2019 | Bannwart |
| 2019/0336346 A1 | 11/2019 | Locke et al. |
| 2019/0336640 A1 | 11/2019 | Vismara et al. |
| 2019/0336641 A1 | 11/2019 | Nisbet |
| 2019/0336643 A1 | 11/2019 | Luukko et al. |
| 2019/0336658 A1 | 11/2019 | Heaton et al. |
| 2019/0336739 A1 | 11/2019 | Locke et al. |
| 2019/0343687 A1 | 11/2019 | Locke et al. |
| 2019/0343889 A1 | 11/2019 | Luukko et al. |
| 2019/0343979 A1 | 11/2019 | Kearney et al. |
| 2019/0343993 A1 | 11/2019 | Weston |
| 2019/0343994 A1 | 11/2019 | Greener |
| 2019/0344242 A1 | 11/2019 | Kim et al. |
| 2019/0350763 A1 | 11/2019 | Pratt et al. |
| 2019/0350764 A1 | 11/2019 | Zochowski et al. |
| 2019/0350765 A1 | 11/2019 | Heagle et al. |
| 2019/0350775 A1 | 11/2019 | Biasutti et al. |
| 2019/0350970 A1 | 11/2019 | Saphier et al. |
| 2019/0351092 A1 | 11/2019 | Silver et al. |
| 2019/0351093 A1 | 11/2019 | Stein et al. |
| 2019/0351094 A1 | 11/2019 | Maher et al. |
| 2019/0351095 A1 | 11/2019 | Maher et al. |
| 2019/0351111 A1 | 11/2019 | Locke et al. |
| 2019/0358088 A1 | 11/2019 | Lavocah et al. |
| 2019/0358361 A1 | 11/2019 | McInnes et al. |
| 2019/0358372 A1 | 11/2019 | Askem et al. |
| 2019/0365948 A1 | 12/2019 | Deegan et al. |
| 2019/0365962 A1 | 12/2019 | Lee et al. |
| 2019/0374408 A1 | 12/2019 | Robles et al. |
| 2019/0374673 A1 | 12/2019 | Hoefinghoff et al. |
| 2019/0380878 A1 | 12/2019 | Edwards et al. |
| 2019/0380881 A1 | 12/2019 | Albert et al. |
| 2019/0380882 A1 | 12/2019 | Taylor et al. |
| 2019/0380883 A1 | 12/2019 | Macphee et al. |
| 2019/0381222 A9 | 12/2019 | Locke et al. |
| 2019/0388577 A1 | 12/2019 | Chandrashekhar-Bhat et al. |
| 2019/0388579 A1 | 12/2019 | Macphee et al. |
| 2019/0388589 A1 | 12/2019 | Macphee et al. |
| 2020/0000640 A1 | 1/2020 | Mondal et al. |
| 2020/0000642 A1 | 1/2020 | Waite |
| 2020/0000955 A1 | 1/2020 | Andrews et al. |
| 2020/0000956 A1 | 1/2020 | Huang et al. |
| 2020/0000985 A1 | 1/2020 | Seddon et al. |
| 2020/0008981 A1 | 1/2020 | Wheldrake |
| 2020/0009289 A1 | 1/2020 | Torabinejad et al. |
| 2020/0009400 A1 | 1/2020 | Ribeiro et al. |
| 2020/0017650 A1 | 1/2020 | Young et al. |
| 2020/0022844 A1 | 1/2020 | Blott et al. |
| 2020/0023102 A1 | 1/2020 | Powell |
| 2020/0023103 A1 | 1/2020 | Joshi et al. |
| 2020/0023104 A1 | 1/2020 | Eriksson et al. |
| 2020/0023105 A1 | 1/2020 | Long et al. |
| 2020/0023106 A1 | 1/2020 | Carroll et al. |
| 2020/0030153 A1 | 1/2020 | Johannison et al. |
| 2020/0030480 A1 | 1/2020 | Choi |
| 2020/0030499 A1 | 1/2020 | Menon et al. |
| 2020/0038023 A1 | 2/2020 | Dunn |
| 2020/0038249 A1 | 2/2020 | Pratt et al. |
| 2020/0038250 A1 | 2/2020 | Edwards et al. |
| 2020/0038251 A1 | 2/2020 | Locke et al. |
| 2020/0038252 A1 | 2/2020 | Spiro |
| 2020/0038283 A1 | 2/2020 | Hall et al. |
| 2020/0038470 A1 | 2/2020 | Datt et al. |
| 2020/0038544 A1 | 2/2020 | Grover et al. |
| 2020/0038546 A1 | 2/2020 | Dizio et al. |
| 2020/0038639 A1 | 2/2020 | Patel et al. |
| 2020/0046565 A1 | 2/2020 | Barta et al. |
| 2020/0046566 A1 | 2/2020 | Carey et al. |
| 2020/0046567 A1 | 2/2020 | Carroll et al. |
| 2020/0046568 A1 | 2/2020 | Sexton |
| 2020/0046663 A1 | 2/2020 | Murdock et al. |
| 2020/0046876 A1 | 2/2020 | Liu |
| 2020/0046887 A1 | 2/2020 | Runquist et al. |
| 2020/0054491 A1 | 2/2020 | Hentrich et al. |
| 2020/0054781 A1 | 2/2020 | Weiser et al. |
| 2020/0060879 A1 | 2/2020 | Edwards et al. |
| 2020/0061253 A1 | 2/2020 | Long et al. |
| 2020/0061254 A1 | 2/2020 | Joshi et al. |
| 2020/0061379 A1 | 2/2020 | Bogie et al. |
| 2020/0064220 A1 | 2/2020 | Locke |
| 2020/0069183 A1 | 3/2020 | Rice et al. |
| 2020/0069476 A1 | 3/2020 | Randolph et al. |
| 2020/0069477 A1 | 3/2020 | Holm et al. |
| 2020/0069478 A1 | 3/2020 | Jabbarzadeh et al. |
| 2020/0069479 A1 | 3/2020 | Buan et al. |
| 2020/0069835 A1 | 3/2020 | Hissink et al. |
| 2020/0069850 A1 | 3/2020 | Beadle et al. |
| 2020/0069851 A1 | 3/2020 | Blott et al. |
| 2020/0069853 A1 | 3/2020 | Hall et al. |
| 2020/0078223 A1 | 3/2020 | Locke et al. |
| 2020/0078224 A1 | 3/2020 | Carroll et al. |
| 2020/0078225 A1 | 3/2020 | Grillitsch et al. |
| 2020/0078305 A1 | 3/2020 | Auvinen et al. |
| 2020/0078330 A1 | 3/2020 | Gay |
| 2020/0078482 A1 | 3/2020 | Yoon et al. |
| 2020/0078499 A1 | 3/2020 | Gadde et al. |
| 2020/0085625 A1 | 3/2020 | Bellini et al. |
| 2020/0085626 A1 | 3/2020 | Braga et al. |
| 2020/0085629 A1 | 3/2020 | Locke et al. |
| 2020/0085630 A1 | 3/2020 | Robinson et al. |
| 2020/0085632 A1 | 3/2020 | Locke et al. |
| 2020/0085991 A1 | 3/2020 | Coomber |
| 2020/0085992 A1 | 3/2020 | Locke et al. |
| 2020/0086014 A1 | 3/2020 | Locke et al. |
| 2020/0086017 A1 | 3/2020 | Jardret et al. |
| 2020/0086049 A1 | 3/2020 | Park et al. |
| 2020/0093646 A1 | 3/2020 | Locke et al. |
| 2020/0093756 A1 | 3/2020 | Sabacinski |
| 2020/0093953 A1 | 3/2020 | Kim et al. |

(56) References Cited

U.S. PATENT DOCUMENTS

| | | |
|---|---|---|
| 2020/0093954 A1 | 3/2020 | Lelse, III |
| 2020/0093970 A1 | 3/2020 | Hunt et al. |
| 2020/0095421 A1 | 3/2020 | Kettel |
| 2020/0095620 A1 | 3/2020 | Kellar et al. |
| 2020/0100945 A1 | 4/2020 | Albert et al. |
| 2020/0101192 A1 | 4/2020 | Folwarzny |
| 2020/0107964 A1 | 4/2020 | Locke et al. |
| 2020/0107965 A1 | 4/2020 | Greener |
| 2020/0107966 A1 | 4/2020 | Francis |
| 2020/0107967 A1 | 4/2020 | Holm et al. |
| 2020/0108169 A1 | 4/2020 | Hu et al. |
| 2020/0113741 A1 | 4/2020 | Rehbein et al. |
| 2020/0114039 A1 | 4/2020 | Wang et al. |
| 2020/0114040 A1 | 4/2020 | Waite et al. |
| 2020/0114049 A1 | 4/2020 | Wall |
| 2020/0121509 A1 | 4/2020 | Locke et al. |
| 2020/0121510 A1 | 4/2020 | Hartwell et al. |
| 2020/0121513 A1 | 4/2020 | Townsend et al. |
| 2020/0121521 A1 | 4/2020 | Daniel et al. |
| 2020/0121833 A9 | 4/2020 | Askem et al. |
| 2020/0129338 A1 | 4/2020 | Gardiner et al. |
| 2020/0129341 A1 | 4/2020 | Coulthard et al. |
| 2020/0129648 A1 | 4/2020 | Drury et al. |
| 2020/0129654 A1 | 4/2020 | Bouvier et al. |
| 2020/0129655 A1 | 4/2020 | Gardiner et al. |
| 2020/0129675 A1 | 4/2020 | Robinson et al. |
| 2020/0138754 A1 | 5/2020 | Johnson |
| 2020/0139002 A1 | 5/2020 | Dudnyk et al. |
| 2020/0139023 A1 | 5/2020 | Haggstrom et al. |
| 2020/0139025 A1 | 5/2020 | Robinson et al. |
| 2020/0141031 A1 | 5/2020 | Kosan et al. |
| 2020/0146894 A1 | 5/2020 | Long et al. |
| 2020/0146896 A1 | 5/2020 | Rice et al. |
| 2020/0146897 A1 | 5/2020 | Locke et al. |
| 2020/0146899 A1 | 5/2020 | Pratt et al. |
| 2020/0155355 A1 | 5/2020 | Hill et al. |
| 2020/0155358 A1 | 5/2020 | Wheldrake |
| 2020/0155359 A1 | 5/2020 | Carroll et al. |
| 2020/0155361 A1 | 5/2020 | Pigg et al. |
| 2020/0155379 A1 | 5/2020 | Shaw et al. |
| 2020/0163802 A1 | 5/2020 | Hunt et al. |
| 2020/0163803 A1 | 5/2020 | Pigg et al. |
| 2020/0164112 A1 | 5/2020 | Kato et al. |
| 2020/0164120 A1 | 5/2020 | Jaecklein et al. |
| 2020/0170841 A1 | 6/2020 | Waite et al. |
| 2020/0170842 A1 | 6/2020 | Locke |
| 2020/0170843 A1 | 6/2020 | Collinson et al. |
| 2020/0171197 A1 | 6/2020 | Hubbell et al. |
| 2020/0179300 A1 | 6/2020 | Urban et al. |
| 2020/0179558 A1 | 6/2020 | Munro et al. |
| 2020/0179673 A1 | 6/2020 | Wan |
| 2020/0188179 A1 | 6/2020 | Bugedo-Albizuri et al. |
| 2020/0188180 A1 | 6/2020 | Akbari et al. |
| 2020/0188182 A1 | 6/2020 | Sanders et al. |
| 2020/0188183 A1 | 6/2020 | Hamerslagh et al. |
| 2020/0188550 A1 | 6/2020 | Dagger et al. |
| 2020/0188564 A1 | 6/2020 | Dunn |
| 2020/0190310 A1 | 6/2020 | Meyer |
| 2020/0197227 A1 | 6/2020 | Locke et al. |
| 2020/0197228 A1 | 6/2020 | Hartwell |
| 2020/0197559 A1 | 6/2020 | Bourdillon et al. |
| 2020/0197580 A1 | 6/2020 | Kilpadi et al. |
| 2020/0206035 A1 | 7/2020 | Kantor et al. |
| 2020/0206036 A1 | 7/2020 | Robinson et al. |
| 2020/0214637 A1 | 7/2020 | Brownhill et al. |
| 2020/0214897 A1 | 7/2020 | Long et al. |
| 2020/0214898 A1 | 7/2020 | Waite et al. |
| 2020/0214899 A1 | 7/2020 | Locke et al. |
| 2020/0215220 A1 | 7/2020 | Schomburg et al. |
| 2020/0215226 A1 | 7/2020 | Kitagawa et al. |
| 2020/0222469 A1 | 7/2020 | Cotton |
| 2020/0229983 A1 | 7/2020 | Robinson et al. |
| 2020/0230283 A1 | 7/2020 | Yang et al. |
| 2020/0237562 A1 | 7/2020 | Rice et al. |
| 2020/0237564 A1 | 7/2020 | Hammond et al. |
| 2020/0237816 A1 | 7/2020 | Lait |
| 2020/0246190 A1 | 8/2020 | Luckemeyer et al. |
| 2020/0246191 A1 | 8/2020 | Lu et al. |
| 2020/0246194 A1 | 8/2020 | Gonzalez et al. |
| 2020/0246195 A1 | 8/2020 | Robinson et al. |
| 2020/0253785 A1 | 8/2020 | Bernet et al. |
| 2020/0253786 A1 | 8/2020 | Harrison et al. |
| 2020/0253788 A1 | 8/2020 | Rehbein et al. |
| 2020/0254139 A1 | 8/2020 | Phillips et al. |
| 2020/0261275 A1 | 8/2020 | Manwaring et al. |
| 2020/0261276 A1 | 8/2020 | Lujan Hernandez et al. |
| 2020/0268560 A1 | 8/2020 | Harrison et al. |
| 2020/0268561 A1 | 8/2020 | Locke et al. |
| 2020/0269028 A1 | 8/2020 | Hegg |
| 2020/0270484 A1 | 8/2020 | Lipscomb et al. |
| 2020/0276055 A1 | 9/2020 | Randolph et al. |
| 2020/0276058 A1 | 9/2020 | Locke et al. |
| 2020/0277450 A1 | 9/2020 | Silverstein et al. |
| 2020/0281519 A1 | 9/2020 | Gowans et al. |
| 2020/0281529 A1 | 9/2020 | Grubb et al. |
| 2020/0281678 A1 | 9/2020 | Long et al. |
| 2020/0281775 A1 | 9/2020 | Kushnir et al. |
| 2020/0282100 A1 | 9/2020 | Gil et al. |
| 2020/0282114 A1 | 9/2020 | Long et al. |
| 2020/0282115 A1 | 9/2020 | Gardner et al. |
| 2020/0289326 A1 | 9/2020 | Nielsen et al. |
| 2020/0289327 A1 | 9/2020 | Hansen et al. |
| 2020/0289328 A1 | 9/2020 | Luckemeyer et al. |
| 2020/0289346 A1 | 9/2020 | Hansen et al. |
| 2020/0289347 A1 | 9/2020 | Gowans et al. |
| 2020/0289701 A1 | 9/2020 | Hall et al. |
| 2020/0289712 A1 | 9/2020 | Jiang et al. |
| 2020/0289723 A1 | 9/2020 | Gregory et al. |
| 2020/0289726 A1 | 9/2020 | Locke et al. |
| 2020/0289727 A1 | 9/2020 | Locke |
| 2020/0289806 A1 | 9/2020 | Locke et al. |
| 2020/0297541 A1 | 9/2020 | Hartwell et al. |
| 2020/0297543 A1 | 9/2020 | Rodzewicz et al. |
| 2020/0297544 A1 | 9/2020 | Moine et al. |
| 2020/0297892 A1 | 9/2020 | Silcock |
| 2020/0297893 A1 | 9/2020 | Ericson |
| 2020/0297894 A1 | 9/2020 | Koyama et al. |
| 2020/0299865 A1 | 9/2020 | Bonnefin et al. |
| 2020/0306089 A1 | 10/2020 | Delury et al. |
| 2020/0306091 A1 | 10/2020 | Lee et al. |
| 2020/0306092 A1 | 10/2020 | Rehbein et al. |
| 2020/0306094 A1 | 10/2020 | Kushnir et al. |
| 2020/0306426 A1 | 10/2020 | Rice et al. |
| 2020/0306428 A1 | 10/2020 | Ingram et al. |
| 2020/0306430 A1 | 10/2020 | Rehbein et al. |
| 2020/0315853 A1 | 10/2020 | Waite |
| 2020/0315854 A1 | 10/2020 | Simmons et al. |
| 2020/0315894 A1 | 10/2020 | Churilla et al. |
| 2020/0316271 A1 | 10/2020 | Lin |
| 2020/0316272 A1 | 10/2020 | Simpson |
| 2020/0316273 A1 | 10/2020 | Hegg |
| 2020/0323692 A1 | 10/2020 | Locke et al. |
| 2020/0324015 A1 | 10/2020 | Kettel et al. |
| 2020/0330283 A1 | 10/2020 | Locke et al. |
| 2020/0330284 A1 | 10/2020 | Locke et al. |
| 2020/0330285 A1 | 10/2020 | Rehbein et al. |
| 2020/0330658 A1 | 10/2020 | Fujisaki |
| 2020/0330660 A1 | 10/2020 | Patel et al. |
| 2020/0337719 A1 | 10/2020 | Ingram et al. |
| 2020/0337904 A1 | 10/2020 | Waite |
| 2020/0337905 A1 | 10/2020 | Earl et al. |
| 2020/0337906 A1 | 10/2020 | Long et al. |
| 2020/0337908 A1 | 10/2020 | Long et al. |
| 2020/0338228 A1 | 10/2020 | Kharkar et al. |
| 2020/0338243 A1 | 10/2020 | Harrison et al. |
| 2021/0162105 A1 | 6/2021 | Coulthard et al. |
| 2021/0220182 A1 | 7/2021 | Locke et al. |
| 2022/0001099 A1 | 1/2022 | Robinson et al. |
| 2022/0047800 A1 | 2/2022 | Johannison et al. |
| 2022/0133545 A1 | 5/2022 | Kieswetter et al. |
| 2022/0168152 A1 | 6/2022 | Locke et al. |

(56) References Cited

U.S. PATENT DOCUMENTS

2022/0183895 A1 6/2022 Regbein et al.
2022/0183896 A1 6/2022 Rehbein et al.

FOREIGN PATENT DOCUMENTS

| | | |
|---|---|---|
| EP | 2514958 A1 | 10/2012 |
| EP | 3187204 A1 | 7/2017 |
| EP | 3556407 A1 | 10/2019 |
| EP | 3569260 A1 | 11/2019 |
| EP | 3643328 A1 | 4/2020 |
| EP | 3643330 A1 | 4/2020 |
| EP | 3643331 A1 | 4/2020 |
| EP | 3669838 A1 | 6/2020 |
| EP | 3669843 A1 | 6/2020 |
| EP | 3669844 A1 | 6/2020 |
| EP | 3434236 B1 | 12/2021 |
| EP | 3946186 | 2/2022 |
| EP | 3968919 | 3/2022 |
| EP | 3968922 | 3/2022 |
| GB | 2579211 A | 6/2020 |
| GB | 2579368 A | 6/2020 |
| JP | 3834523 B2 | 10/2006 |
| WO | 2005018543 A2 | 3/2005 |
| WO | 2011121394 A1 | 10/2011 |
| WO | 2011135284 | 11/2011 |
| WO | 2011144888 A1 | 11/2011 |
| WO | 2013015827 A2 | 1/2013 |
| WO | 2013126049 A1 | 8/2013 |
| WO | 2014014842 A1 | 1/2014 |
| WO | WO-2014158529 A1 * 10/2014 ....... A61F 13/00068 | |
| WO | 2015145117 A1 | 10/2015 |
| WO | 2015173546 A1 | 11/2015 |
| WO | 2016141450 A1 | 9/2016 |
| WO | 2017016974 A1 | 2/2017 |
| WO | 2017125250 A1 | 7/2017 |
| WO | 2018029231 A1 | 2/2018 |
| WO | 2018094061 A1 | 5/2018 |
| WO | 2018162613 A1 | 9/2018 |
| WO | 2018163093 A1 | 9/2018 |
| WO | 2018189265 A1 | 10/2018 |
| WO | 2018226667 A1 | 12/2018 |
| WO | 2018227144 A1 | 12/2018 |
| WO | 2018231825 A1 | 12/2018 |
| WO | 2018236648 A1 | 12/2018 |
| WO | 2019002085 A1 | 1/2019 |
| WO | 2019012068 A1 | 1/2019 |
| WO | 2019012069 A1 | 1/2019 |
| WO | 2019022493 A1 | 1/2019 |
| WO | 2019027933 A1 | 2/2019 |
| WO | 2019038548 A1 | 2/2019 |
| WO | 2019038549 A1 | 2/2019 |
| WO | 2019040656 A1 | 2/2019 |
| WO | 2019050855 A1 | 3/2019 |
| WO | 2019058373 A1 | 3/2019 |
| WO | 2019073326 A1 | 4/2019 |
| WO | 2019083563 A1 | 5/2019 |
| WO | 2019083868 A1 | 5/2019 |
| WO | 2019086911 A1 | 5/2019 |
| WO | 2019091150 A1 | 5/2019 |
| WO | 2019094147 A1 | 5/2019 |
| WO | 2019096828 A1 | 5/2019 |
| WO | 2019113091 A1 | 6/2019 |
| WO | 2019113275 A1 | 6/2019 |
| WO | 2019113623 A1 | 6/2019 |
| WO | 2019193141 A1 | 10/2019 |
| WO | 2019193333 A1 | 10/2019 |
| WO | 2019199389 A1 | 10/2019 |
| WO | 2019199596 A1 | 10/2019 |
| WO | 2019199687 A1 | 10/2019 |
| WO | 2019199798 A1 | 10/2019 |
| WO | 2019199849 A1 | 10/2019 |
| WO | 2019200035 A1 | 10/2019 |
| WO | 2019215572 A1 | 11/2019 |
| WO | 2019219613 A1 | 11/2019 |
| WO | 2019234365 A1 | 12/2019 |
| WO | 2020005062 A1 | 1/2020 |
| WO | 2020005344 A1 | 1/2020 |
| WO | 2020005536 A1 | 1/2020 |
| WO | 2020005546 A1 | 1/2020 |
| WO | 2020005577 A1 | 1/2020 |
| WO | 2020007429 A1 | 1/2020 |
| WO | 2020011691 A1 | 1/2020 |
| WO | 2020014178 A1 | 1/2020 |
| WO | 2020014310 A1 | 1/2020 |
| WO | 2020018300 A1 | 1/2020 |
| WO | 2020026061 A1 | 2/2020 |
| WO | 2020026144 A1 | 2/2020 |
| WO | 2020033351 A1 | 2/2020 |
| WO | 2020035811 A1 | 2/2020 |
| WO | 2020043665 A1 | 3/2020 |
| WO | 2020044237 A1 | 3/2020 |
| WO | 2020046443 A1 | 3/2020 |
| WO | 2020047255 A1 | 3/2020 |
| WO | 2020049038 A1 | 3/2020 |
| WO | 2020055945 A1 | 3/2020 |
| WO | 2020056014 A1 | 3/2020 |
| WO | 2020056182 A1 | 3/2020 |
| WO | 2020065531 A1 | 4/2020 |
| WO | 2020070231 A1 | 4/2020 |
| WO | 2020074512 A1 | 4/2020 |
| WO | 2020078993 A1 | 4/2020 |
| WO | 2020079009 A1 | 4/2020 |
| WO | 2020079330 A1 | 4/2020 |
| WO | 2020081259 A1 | 4/2020 |
| WO | 2020081391 A1 | 4/2020 |
| WO | 2020092598 A1 | 5/2020 |
| WO | 2020136555 A1 | 7/2020 |
| WO | 2020141059 A1 | 7/2020 |
| WO | 2020144347 A1 | 7/2020 |
| WO | 2020150548 A1 | 7/2020 |
| WO | 2020159675 A1 | 8/2020 |
| WO | 2020159677 A1 | 8/2020 |
| WO | 2020159678 A1 | 8/2020 |
| WO | 2020159823 A1 | 8/2020 |
| WO | 2020159859 A1 | 8/2020 |
| WO | 2020159892 A1 | 8/2020 |
| WO | 2020161086 A1 | 8/2020 |
| WO | 2020173665 A1 | 9/2020 |
| WO | 2020173760 A1 | 9/2020 |
| WO | 2020174264 A1 | 9/2020 |
| WO | 2020174510 A1 | 9/2020 |
| WO | 2020182887 A1 | 9/2020 |
| WO | 2020197759 A1 | 10/2020 |
| WO | 2020197760 A1 | 10/2020 |
| WO | 2020198484 A1 | 10/2020 |
| WO | 2020201879 A1 | 10/2020 |
| WO | 2020213998 A1 | 10/2020 |
| WO | 2019191590 A1 | 10/2021 |

\* cited by examiner

LOW PROFILE FILTER DEVICES SUITABLE FOR USE IN NEGATIVE PRESSURE WOUND THERAPY SYSTEMS

BACKGROUND

Fluid filters in various medical applications suffer from various limitations, some of which relate to resistance of fluid flow caused by the filter. For example, in fluid systems in which large volumes of fluid are passed through a filter, the rate at which the fluid passes through the filter is limited by several factors, such as, for example, the physical properties of the filter material, the physical properties of the fluid and the surface area of the filter that is available for passage of the fluid therethrough. These and other limitations can cause a build-up of pressure at the filter site and can cause unacceptable levels of fluid backup due to the flow rate characteristics of the filter.

In regards to a filter that is designed to for use in the filtering of a fluid flowing through a conduit, such as a catheter, a syringe, rubber tubing and the like, such a filter is conventionally provided in the form of a device that is fluidly connected to the conduit, also referred to herein as a "filter adaptor," which situates a filter within the fluid flow path in an orientation perpendicular to the direction in which the fluid flows. A conventional way to improve flow of fluid through such a filter is to increase the surface area of the filter by increasing the diameter of the filter, thereby increasing the surface area of the filter that is operable to permit passage of the fluid being filtered. Increasing the diameter of a filter and/or a filter adaptor, however, creates problems in many applications of such filters. For example, when a filter adaptor is used in connection with fluid flow tubing of a fluid system that requires tubing to lie in contact with a patient's skin or in which the adaptor is to be positioned on tubing between a wound dressing and a pump, as would occur in a negative pressure wound therapy system, the increased diameter of a filter adaptor is undesirable because the filter adaptor can become unwieldy, causing pressure damage to the patient's skin or other tissues away from the wound site and/or become entangled with the patient's clothing, which could cause damage to clothing and/or possibly disturb the wound. This can not only cause pain to the patient, but in the case of negative pressure wound therapy, can dislodge a dressing or otherwise cause a reduction in vacuum under the dressing.

In view of the above, there is a need for fluid filter systems that have a low profile and filter adaptors that are sufficiently compact to minimize impact to a patient while also filtering a flow of fluid at an acceptable rate while minimizing pressure drop across the filter. The present disclosure addresses these needs.

SUMMARY

The present disclosure provides low profile filter devices suitable for use in negative pressure wound therapy systems and in other systems in which fluid filtering is desired. In one aspect of the disclosure, there is provided a filter adaptor that includes (i) a body that defines an internal passageway disposed between an inlet and an outlet, the passageway configured to permit passage of a fluid in a first direction defined by the inlet and the outlet; and (ii) a filter disposed within the passageway and oriented to define a volumetric direction that is different than the first direction. In some embodiments, the volumetric direction is perpendicular to the first direction. In some embodiments, the volumetric direction and the first direction are offset by an angle of at least 15°.

In some embodiments, the filter adaptor has a tubular shape and has an outside diameter, and the filter has a surface area that is independent of the outside diameter. In some embodiments, the outside diameter is from about 3 mm to about 15 mm.

In some embodiments, the filter is cylindrical. In some embodiments, the filter is planar. In some embodiments, the filter lies on a plane that is not perpendicular to the first direction. In some embodiments, the filter lies on a plane that forms an angle with the first direction, and wherein the angle is less than 45°. In some embodiments, the filter comprises gas permeable material. In some embodiments, the filter comprises liquid impermeable material. In some embodiments, the filter is gas permeable and liquid impermeable. In some embodiments, the filter is hydrophobic.

In some embodiments, the body includes a first connector at the inlet and a second connector at the outlet. In some embodiments, each of the first connector and the second connector comprises a barb, hose, or luer connector. In some embodiments, the filter adaptor further comprises an indicator positioned within the internal passageway. In some embodiments, the indicator detects blockage or detects a need for a dressing change. In some embodiments, the indicator sensor comprises symbols, letters, numbers, or a color change.

In another aspect of the disclosure, there is provided a filter adaptor that includes (i) a body that defines an internal passageway disposed between an inlet and an outlet, and (ii) a filter disposed within the passageway, wherein the filter comprises a gelling absorbent material that, when in a dry state, is permeable to gas and that, when contacted by an aqueous fluid, converts to a gel. In some embodiments, the gelling absorbent material comprises a gel-forming fiber. In some embodiments, the gelling absorbent material comprises a compressed gel-forming fiber. In some embodiments, the compressed gel-forming fiber has a density of from about 10 to about 70 kg/cm$^3$. In some embodiments, the internal passageway comprises a spiral path.

Further features, characteristics and embodiments of the present disclosure will be apparent from the detailed description herein.

INCORPORATION BY REFERENCE

All publications, patents, and patent applications mentioned in this specification are herein incorporated by reference to the same extent as if each individual publication, patent, or patent application was specifically and individually indicated to be incorporated by reference.

Figure 1:
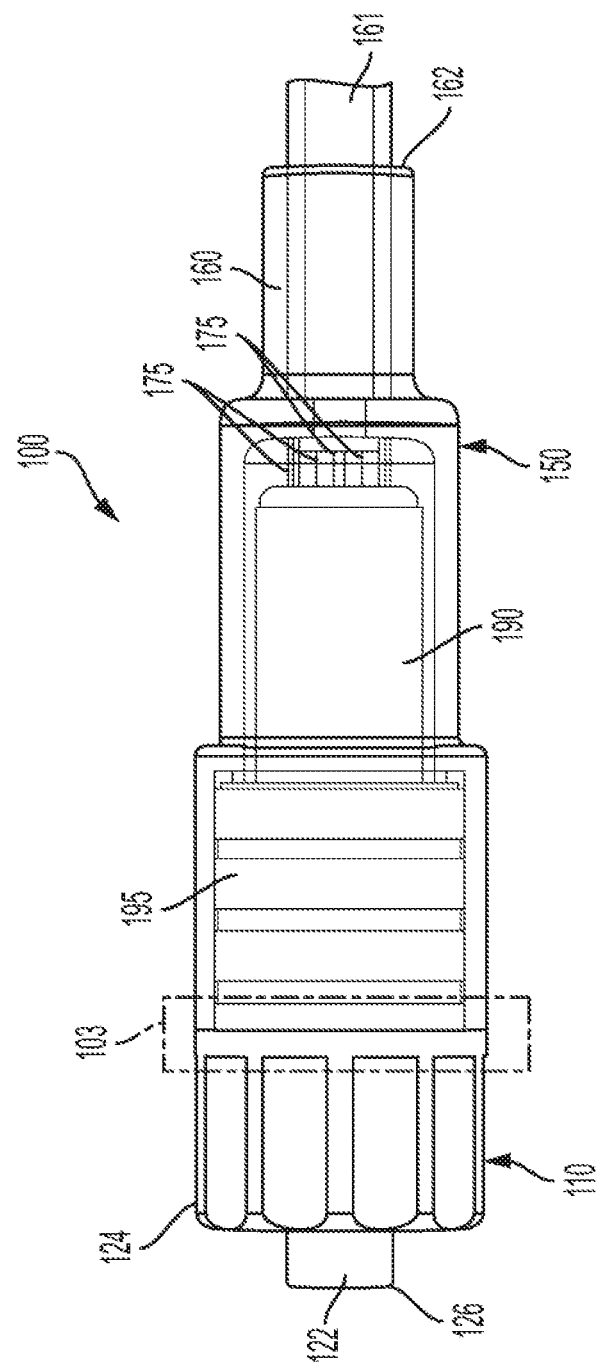
FIG. 1 shows a side elevation view of one filter adaptor embodiment in accordance with the disclosure.

It should be understood that the drawings are not necessarily to scale and that the disclosed embodiments are sometimes illustrated diagrammatically and in partial views. In certain instances, details which are not necessary for an understanding of the disclosed methods and devices or which render other details difficult to perceive may have been omitted. It should be further understood that this disclosure is not limited to the particular embodiments illustrated herein.

DESCRIPTION

For the purposes of promoting an understanding of the principles of the invention, reference will now be made to the embodiments described herein and illustrated in the Figures and specific language will be used to describe the same. The embodiments of the present application described below are not intended to be exhaustive or to limit the teachings of the present application to the precise forms disclosed in the following detailed description. Rather, the embodiments are chosen and described so that others skilled in the art may appreciate and understand the principles and practices of the present application. It will therefore be understood that no limitation of the scope of the invention is intended by the description of specific embodiments. Any alterations and further modifications in the described embodiments, and any further applications of the principles of the invention as described herein are contemplated as would normally occur to one skilled in the art to which the invention relates.

Described herein are compact filter devices for use with medical equipment, including wound dressings and other negative pressure wound therapy equipment, which are capable of filtering large volumes of fluid. While the specific embodiments described herein are configured as filter adaptors that can be connected to, or positioned within, a fluid conduit, it is to be understood that this disclosure also contemplates that the filter devices alternatively can be constructed as a part of a fluid conduit or other device that defines a fluid flow path as a unitary construct. As a corollary, while various filter adaptor embodiments described herein include structures for engaging the filter adaptors to a conduit, such as luer connectors, barb fittings and connectors of various other types, it is to be understood that embodiments in which filter devices that are constructed as an integral part of a fluid conduit or other device that defines a fluid flow path would omit such connectors.

In various filter adaptor embodiments and method and process embodiments disclosed herein, filtering capacity of filter adaptors having generally tubular design under a given set of conditions, such as, for example, pressure, flow volume and the like, can be increased by increasing the tube length, which correspondingly increases the operational surface area of the filter, without changing the diameter of the filter adaptor. In other embodiments, adaptor filters having features as described herein can have other elongated shapes without departing from the principles of the disclosure, such as elongated shapes having outer cross-sectional shapes that are elliptical, square, triangular, circular or rectangular.

Throughout this disclosure, various quantities, such as amounts, sizes, dimensions, proportions and the like, are presented in a range format. It should be understood that the description of a quantity in range format is merely for convenience and brevity and should not be construed as an inflexible limitation on the scope of any embodiments. Accordingly, the description of a range should be considered to have specifically disclosed all the possible subranges as well as individual numerical values within that range unless the context clearly dictates otherwise. For example, description of a range such as from 1 to 6 should be considered to have specifically disclosed subranges such as from 1 to 3, from 1 to 4, from 1 to 5, from 2 to 4, from 2 to 6, from 3 to 6, from 1.2 to 5.2, from 1.25 to 5.25 etc., as well as individual values within that range, for example, 1.1, 2, 2.3, 2.33, 2.35, 5, and 5.9. This applies regardless of the breadth of the range. The upper and lower limits of these intervening ranges may independently be included in the smaller ranges, and are also encompassed within the disclosure, subject to any specifically excluded limit in the stated range. Where the stated range includes one or both of the limits, ranges excluding either or both of those included limits are also included in the disclosure, unless the context clearly dictates otherwise.

The terminology used herein is for the purpose of describing particular embodiments only and is not intended to be limiting of any embodiment. As used herein, the singular forms "a," "an" and "the" are intended to include the plural forms as well, unless the context clearly indicates otherwise. It will be further understood that the terms "includes", "comprises", "including" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed herein could be termed a second element, component, region, layer or section without departing from the teachings of the example embodiments.

As used herein, ranges and amounts can be expressed as "about" a particular value or range. About also includes the exact amount. For example, "about 5 µL" means "about 5 µL" and also "5 µL." Generally, the term "about" includes an amount that would be expected to be within experimental error. The term "about" includes values that are within 10% less to 10% greater of the value provided. For example, "about 50%" means "between 45% and 55%." Also, by way of example, "about 30" means "between 27 and 33."

Described herein, in certain embodiments, are filter adaptors for filtering unwanted particulates during various uses including in conjunction with negative pressure wound therapy and syringes. In some embodiments, filter adaptors are provided that have generally tubular design. In some embodiments, filter adaptors are provided that are configured for in-line connection to two fluid conduits or two separated portions of a fluid conduit. In other embodiments, filter adaptors having generally tubular design are provided that are sized to be positioned inside a fluid conduit. Filter adaptors having generally tubular design according to various embodiments described herein are characterized by having a ratio of outside diameter to filter surface area that is lower than conventional filter adaptors, and which have designs that can be readily modified to provide filter adaptors having increased filter surface areas by increasing the length of a filter adaptor without increasing the overall diameter of the design. As will be understood by a person skilled in the art, increased filter surface area enables filtering of larger fluid volumes and/or filtering fluids at a greater volumetric rate and/or reduced pressure drop across the filter compared to a filter having a lower surface area.

In one aspect of the disclosure, a filter adaptor defines an internal fluid passageway, includes a first connector situated at a first end of the filter adaptor configured for connection to a first conduit for fluid delivery into the fluid passageway and a second connector situated at a second end of the filter adaptor configured for connection to a second conduit for fluid flow out of the fluid passageway, wherein the overall flow of fluid is generally in a first direction extending from the first connector to the second connector. In some examples in which the filter adaptor is a generally tubular filter adaptor, the first direction is generally parallel to a longitudinal axis of the filter adaptor. The filter adaptor also includes a filter disposed within the passageway such that all fluid flowing through the passageway passes through the filter, and such that fluid passes through the filter in a volumetric direction that is different from the first direction. As used herein, the term "volumetric direction" is used to refer to a direction that a volume of fluid moves as it crosses a filter, and is generally perpendicular to the filter surface at a given point on the filter. In some embodiments, the volumetric direction is not parallel to the first direction. In other embodiments, the volumetric direction is perpendicular to the first direction. In yet other embodiments, the volumetric direction forms a non-zero angle relative to the first direction, which is referred to herein as an "offset angle." In some embodiments, the offset angle is an angle of at least about 15°, an angle of at least 30°, an angle of at least 45°, an angle of at least 60° or an angle of at least 75°.

Positioning a filter in such a way within a filter adaptor, which causes a fluid to pass through the filter in a direction different than the general direction of fluid flow through the adaptor, enables design modifications that increase filter surface area without increasing external dimensions, such as a diameter, of such filter adaptors.

A representative embodiment of a filter adaptor according to this aspect is depicted in FIGS. 1-11. Filter adaptor 100 includes main body 110 configured for engagement with housing 150 to form a fluid flow path extending from inlet port 162 of housing 150, positioned at a first end of filter adaptor 100 to outlet port 126 of main body 120, positioned at a second end of filter adaptor 100. In some embodiments, connector 120 is configured to connect to a pump unit (not shown) such as one used for negative pressure wound therapy or to a tube (not shown) that is, in turn, connected to a pump unit. In FIG. 1, connector 160 is shown connected to a tube 161. Filter adaptor 100 further includes filter 190, which, in this embodiment, has a cylindrical shape as more clearly seen in FIGS. 5 and 6 and indicator 195 Indicator 195 is operable to indicate a state of filter adaptor 100, such as, for example, an indicator for blockage or a dressing change indicator. In some embodiments, a one way valve (not shown) is located before or after the filter relative to the direction of fluid flow through filter adaptor 100.

In some embodiments, the indicator is used as a dressing change indicator or a blockage indicator. In some embodiments, the indicator is a pH level indicator. In some embodiments, the filter adaptor comprises a plurality of indicators. In some embodiments, the filter adaptor comprises a first indicator for dressing change and a second indicator for blockage detection. In some embodiments, one or more stripes are used for the plurality of indicators.

The indicator for use with filter adaptors as described herein, in some embodiments, is a visual indicator. In some embodiments, the indicator demonstrates a change by a change in appearance of the indicator. For example, the change is a change in color. In some embodiments, the change in color is a color change of a line. In some embodiments, the line is horizontal, vertical, or circular. In some embodiments, the indicator comprises symbols, letters, or numbers for indicating a change.

In some embodiments, a one-way-valve is formed integrally into a filter adaptor, such as, for example, at a location indicated by box 103. In other embodiments, a one-way valve is connected as a separate unit to filter adaptor 100, either directly or by way of an intervening conduit such as a tube, either upstream or downstream of filter adaptor 100 relative to the direction of fluid flow therethrough. The filter adaptors as described herein comprise, in certain embodiments, a valve. In some embodiments, the valve is a one-way valve. In some embodiments, the valve is located before the filter. In some embodiments, the valve is located after the filter. The valve may comprise a check valve cartridge. In some embodiments, the check valve cartridge comprises a hydrocarbon polymer. Representative examples of hydrocarbon polymers include, but are not limited to, polyethylene, polypropylene, polystyrene, derivatives thereof, or combinations thereof. In some embodiments, the check valve cartridge comprises polystyrene. In some embodiments, the valve comprises a check valve disk. In some embodiments, the check valve disk comprises a polysiloxane, also referred to herein as silicone.

Tubular filter 190, in some embodiments, comprises a gas permeable material. In some embodiments, the filter is hydrophobic. In some embodiments, the filter is liquid impermeable. In some embodiments, the filter is both gas permeable and liquid impermeable. In some embodiments, the filter comprises material that is gas permeable and liquid permeable. Representative examples of materials include, but are not limited to, polytetrafluoroethylene (PTFE), polypropylene, and polyethylene. In some embodiments, the material is microporous. In some embodiments, the material comprises a pore size of at least or about 0.01 uM, 0.02 uM, 0.03 uM, 0.04 uM, 0.05 uM, 0.1 uM, 0.2 uM, 0.3 uM, 0.4 uM, 0.5 uM, 0.6 uM, 0.7 uM, 0.8 uM, 0.9 uM, 1.0 uM, or more than 1.0 uM. In some embodiments, the material comprises a pore size in a range of about 0.01 uM to about 1.0 uM, about 0.02 uM to about 0.9 uM, about 0.03 uM to about 0.8 uM, about 0.04 uM to about 0.7 uM, about 0.05 to about 0.6 uM, or about 0.1 uM to about 0.4 uM. In some embodiments, the material comprises a pore size of about 0.2 uM.

In various embodiments, each of connector 120 and connector 160 may comprise any one of a barb, hose, luer (e.g. male or female) connector or other type of connector as would occur to a person of ordinary skill in the art.

Figure 2:
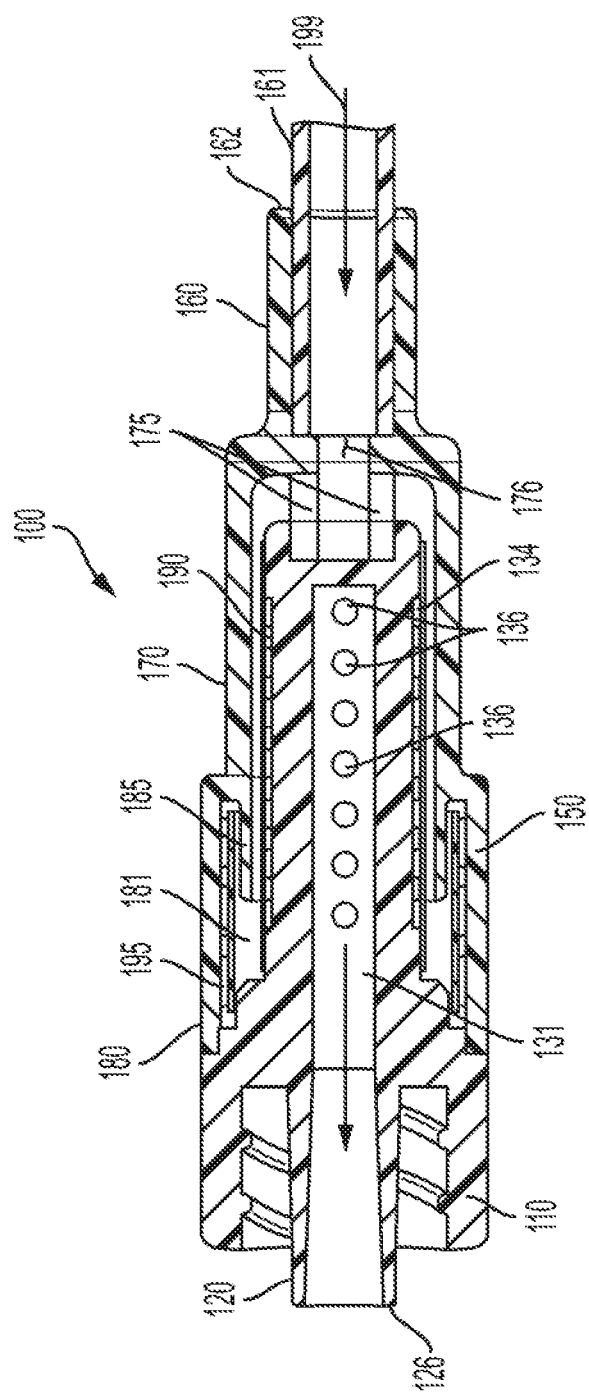
FIG. 2 is a cross-sectional view of the filter adaptor embodiment shown in FIG. 1.
Figure 3:
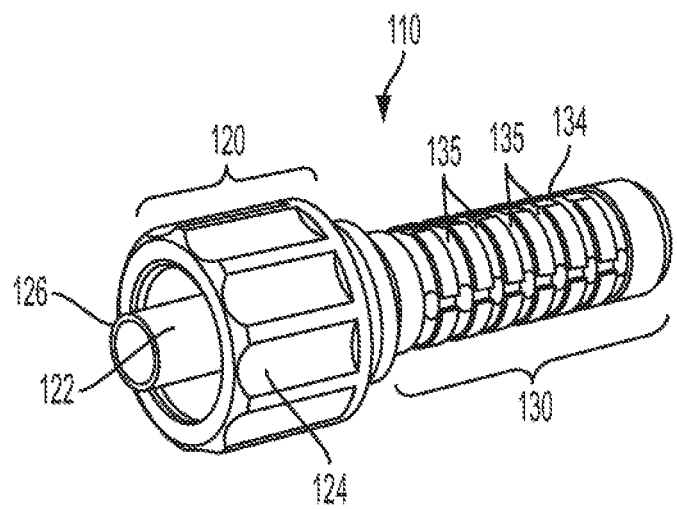
FIG. 3 is a perspective view of the main body of the filter adaptor embodiment shown in FIG. 1.
Figure 4:
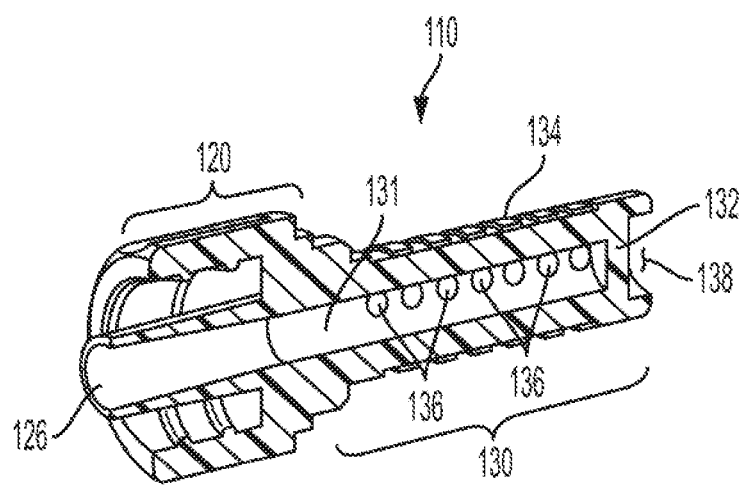
FIG. 4 is a cross-sectional view of the main body of the filter adaptor embodiment shown in FIG. 1.

A cross section of filter adaptor 100 is shown in FIG. 2. As shown in FIG. 2, and with further reference to FIGS. 3 and 4, main body 110 of filter adaptor 100 includes connector 120 and shaft 130. Connector 120 is configured as a luer connector and includes center mounting bore 122, which defines outlet port 126, and hub 124 which, in this embodiment, is configured with threading on an inner surface thereof to engage a threaded collar of a male luer fitting, and ribbing on an outer surface thereof to assist a user with gripping connector 120. Shaft 130 is configured for insertion into a chamber defined in housing 150, as described further below. Shaft 130 defines passageway 131 that extends from end wall 132, through shaft 130, and extends through connector 120 to outlet port 126. Shaft 130 extends distally beyond end wall 132 a short distance, thereby forming recess 138 to receive flanges 175 of housing 150, as described further below. Shaft 130 has outer surface 134 that defines grooves 135 and includes holes 136 that provide fluid communication between grooves 135 and passageway 131. While grooves 135 are shown in this embodiment as being oriented circumferentially around shaft 130, this disclosure contemplates other orientations for grooves 135 such as, for example, spiral or helical grooves, longitudinal grooves and mesh-cut grooves.

Figure 5:
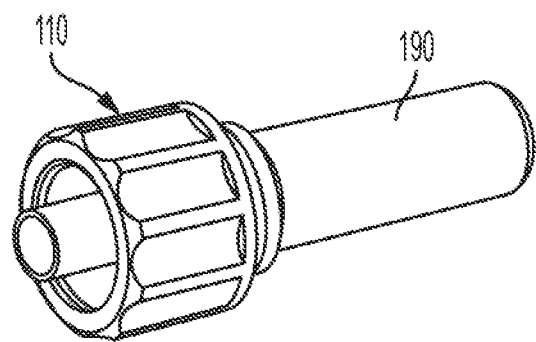
FIG. 5 is a perspective view of the main body and the filter of the filter adaptor embodiment shown in FIG. 1.
Figure 6:
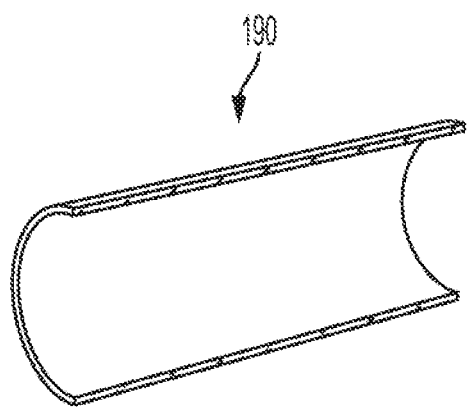
FIG. 6 is a cross-sectional view of the filter of the filter adaptor embodiment shown in FIG. 1.
Figure 7:
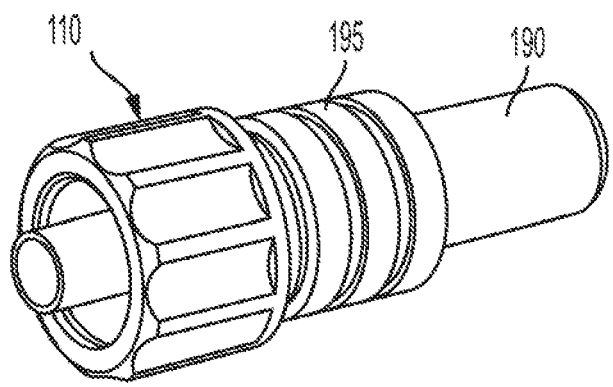
FIG. 7 is a perspective view of the main body, the filter and the indicator of the filter adaptor embodiment shown in FIG. 1.
Figure 8:
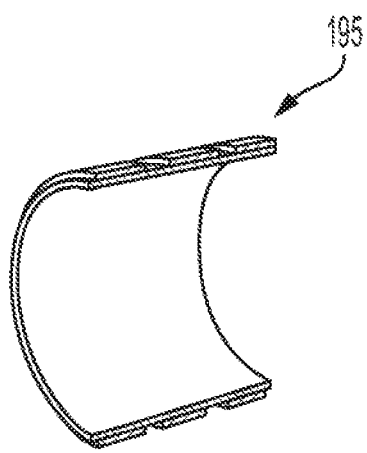
FIG. 8 is a cross-sectional view of the indicator of the filter adaptor embodiment shown in FIG. 1.

As shown in FIG. 1, and with further reference to FIGS. 5 and 6, filter adaptor 100 further includes filter 190 configured for placement over, and in contact with outer surface 134 of shaft 130. In the embodiment shown, filter 190 is cylindrical.

Figure 9:
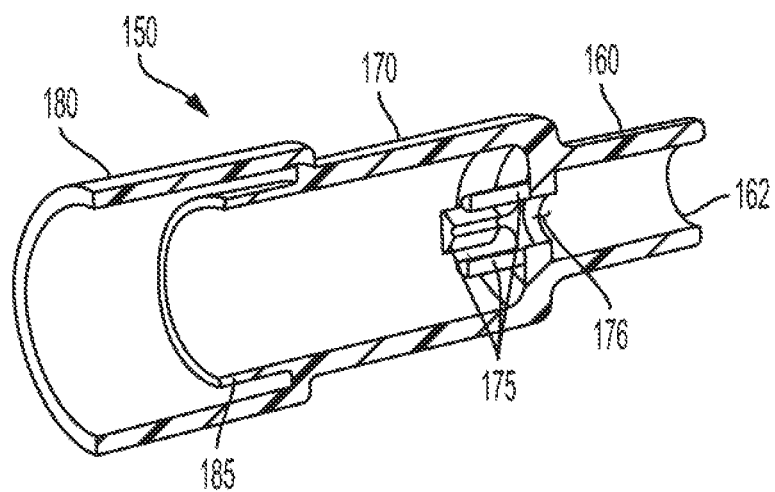
FIG. 9 is a cross-sectional view of the housing of the filter adaptor embodiment shown in FIG. 1.
Figure 10:
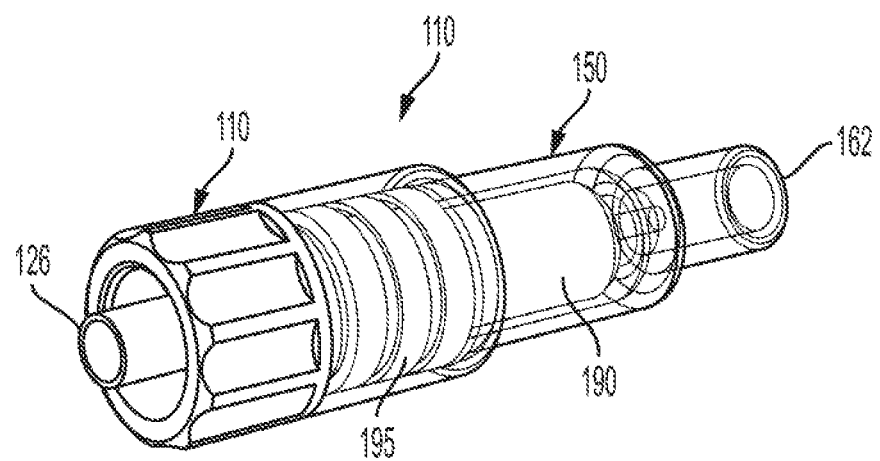
FIG. 10 is a perspective view of the filter adaptor embodiment shown in FIG. 1.
Figure 11:
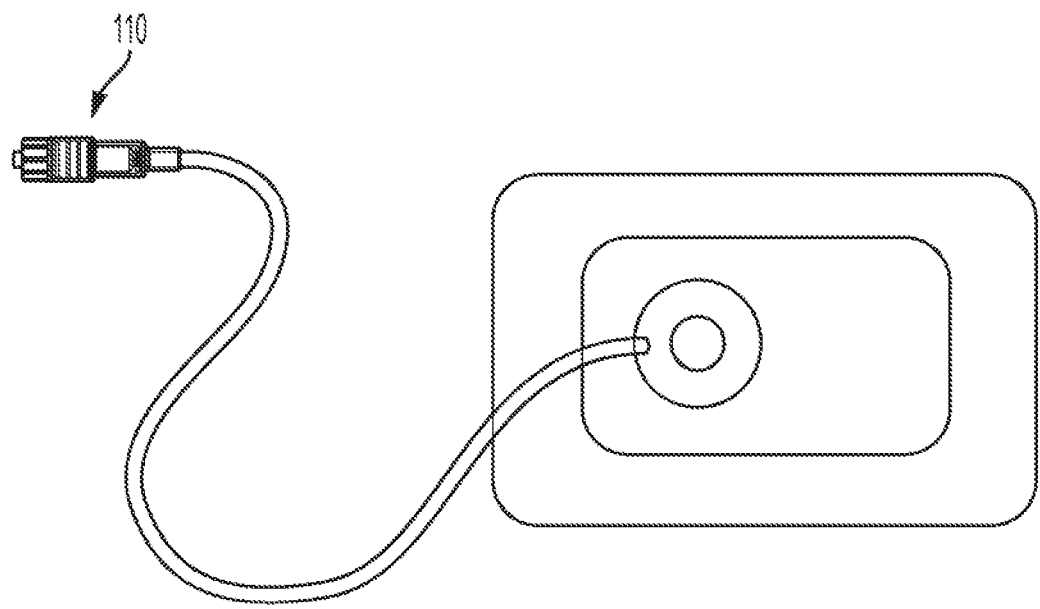
FIG. 11 shows the filter adaptor embodiment of FIG. 1 connected to a wound dressing.

As shown in FIG. 2, and with further reference to FIGS. 9 and 10, filter adaptor 100 also includes housing 150 that is configured to connect with main body 110 to defined a fluid pathway from inlet port 162 to outlet port 126 of filter adaptor 100. Housing 150 includes connector 160 defining inlet port 162 and configured to connect with tube 161. Housing 150 also includes intermediate side wall 170 that defines an intermediate chamber within housing 150 for receiving shaft 130 of main body 110 when housing 150 and main body 110 are connected with one another. Intermediate side wall 170 is sized such that its inner surface is spaced apart from filter 190 when shaft 130 and filter 190 are positioned therein.

Housing 150 also includes flanges 175 configured to seat within recess 138 formed in shaft 130 when housing 150 and main body 110 are connected to one another, thereby maintaining shaft 130 centered within the intermediate chamber, which in turn maintains proper spacing to maintain a fluid flow path within filter adaptor 100 as described further below. Aperture 176 is defined between connector 160 and the intermediate chamber between flanges 175.

Housing 150 also includes outer side wall 180 that is configured to engage main body 110 and also to provide a fluid collection space 181 between outer side wall 180 and shaft 130 of main body 110. In the embodiment shown, housing also includes a circumferential collar 185 extending into the fluid collection space and defining a slot for retaining indicator 195 within the fluid collection space, as most clearly seen in FIGS. 1 and 2. In other embodiments, not shown, collar 185 and indicator 195 are absent.

With reference again to FIG. 2, arrows 199 show the fluid flow path into inlet port 162, through filter adaptor 100 and out through outlet port 126. More specifically, arrows 199 show directions of fluid flow in various areas of filter adaptor 100 from inlet port through connector 160, and through the aperture between connector 160 and the intermediate chamber, where it is redirected in a lateral direction through flanges 175 toward outer surface 134 of shaft 130. The fluid flow path is then again redirected by intermediate side wall 170 of housing 150 to flow toward the fluid collection space and indicator 195 of this embodiment. Within the intermediate cavity and the fluid collection space, the fluid flow path is again redirected toward passageway 131, and travels into passageway 131 by passing through filter 190 into grooves 135, then through holes 136 into passageway 131, where it is again redirected toward outlet port 126.

In the embodiment shown, fluid flow is achieved in the direction of arrows 199 by application of a pressure gradient across filter adaptor 100 that is sufficient to pass the fluid through filter 190. Pressure may be applied by exerting a positive pressure on the inlet port side of filter adaptor 100 or by applying a negative pressure (i.e., suction) on the outlet port side of filter adaptor 100. Moreover, due to the construction of filter adaptor 100, it can be operated equally well with a fluid flow in the opposite direction of that described above, in which case outlet port 126 operates as an inlet port and inlet port 162 operates as an outlet port. When filter adaptor 100 or a variant thereof is used in this opposite direction, indicator 195 and collar 185 can be omitted. Of course, in an embodiment that omits indicator 195, a user may employ a separate indicator unit by positioning an indicator upstream of the filter adaptor (i.e., between the filter adaptor and the wound dressing, or "pre-filter").

As will be appreciated by a person of ordinary skill, an adaptor having features similar to adaptor 100 can be constructed to significantly increase the surface area of filter 190 without increasing the outside diameter of the adaptor by simply increasing the length of adaptor 100 and increasing the length of filter 190. Elongating filter 190 increases the surface area of filter 190 that is available for passage of the fluid without increasing the outer profile of the filter adaptor.

Figure 12:
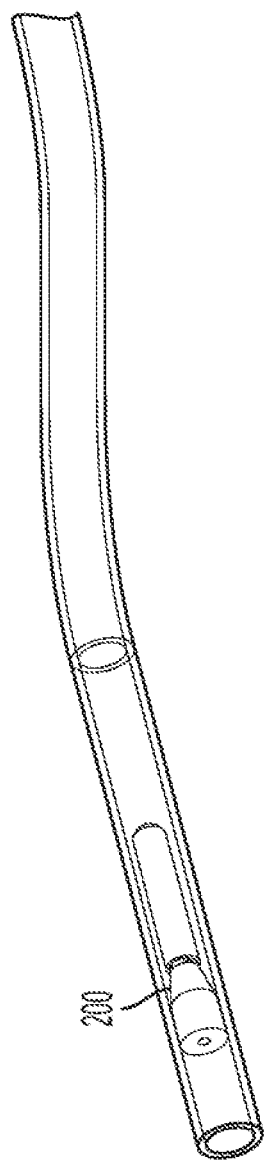
FIG. 12 is a perspective view of another filter adaptor embodiment according to the present disclosure inside a tube.
Figure 13:
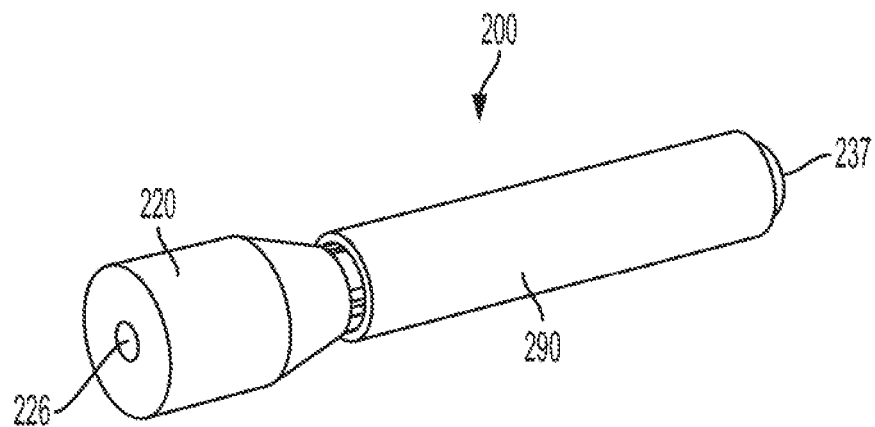
FIG. 13 is a perspective view of the filter adaptor embodiment shown in FIG. 12.
Figure 14:
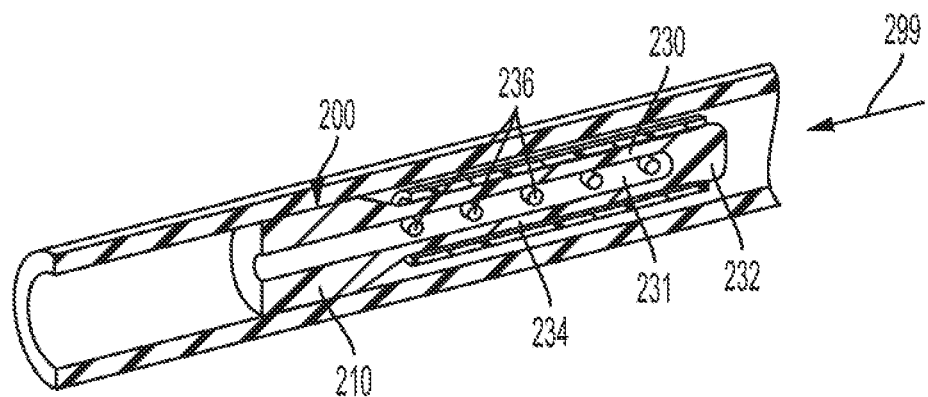
FIG. 14 is a cross-sectional view of the filter adaptor embodiment shown in FIG. 12 inside a tube.

Another representative embodiment of a filter adaptor according to this aspect of the disclosure is depicted in FIGS. 12-14. Filter adaptor 200 differs from filter adapter 100 in that filter adaptor 200 does not include a housing, does not include connectors and is not configured for attachment to conduits as is filter adaptor 100. Rather filter adaptor 200 is configured to be positioned within a lumen of a conduit to filter a fluid that flows through the conduit. Filter adaptor 200 includes main body 210 configured for frictional engagement with a lumen wall of a conduit in which filter adaptor 200 is inserted.

Main body 210 of filter adaptor 200 includes seal 220 and shaft 230. Seal 220 has an outer dimension approximating the lumen dimension of a conduit in which filter adaptor 200 is to be positioned for use and defines outlet port 226. If desired, seal 220 may include circumferential ribbing on an outer surface thereof (not shown) to assist with frictional engagement of seal 220 to the lumen. Shaft 230 of main body 210 has an outer dimension less than the lumen dimension of a conduit in which filter adaptor 200 is to be positioned for use. Shaft 230 defines passageway 231 that extends from end wall 232, through shaft 230, and extends through seal 220 to outlet port 226. Shaft 230 has outer surface 234 that defines grooves 235 similar to grooves 135 in filter adaptor 100 and includes holes 236 that provide fluid communication between grooves 235 and passageway 231.

Filter adaptor 200 further includes filter 290 configured for placement over, and in contact with outer surface 234 of shaft 230. In the embodiment shown, filter 290 is cylindrical. In one embodiment (not shown), main body 210 also includes flanges 275 extending laterally from distal end 237 of shaft 230, which operate to hold filter 290 in position relative to shaft 230 and also to maintain end 237 of shaft 230 centered within the lumen into which filter adaptor is inserted, which in turn maintains proper spacing to maintain a fluid flow path between filter 290 and the wall of the lumen.

Fluid flow in the lumen is in the direction indicated by arrow 299. As fluid reaches filter adaptor 200, it passes between filter 290 and the wall of the lumen toward seal 220. Within the space between the filter and the lumen wall, the fluid flow path is redirected toward passageway 231, and travels into passageway 231 by passing through filter 290 into grooves 235, then through holes 236 into passageway 231, where it is again redirected toward outlet port 226.

In the embodiment shown, fluid flow is achieved in the direction of arrow 299 by application of a pressure gradient across filter adaptor 200 that is sufficient to pass the fluid through filter 290. Pressure may be applied by exerting a positive pressure on the upstream side of filter adaptor 200 or by applying a negative pressure (i.e., suction) on the downstream side of filter adaptor 200. Moreover, due to the construction of filter adaptor 200, it can be operated equally well with a fluid flow in the opposite direction of that described above, in which case outlet port 226 operates as an inlet port, fluid flows into inlet port 226, through passageway 231, through holes 236, into grooves 235, then through filter 290 before continuing through the lumen in the direction opposite that of arrow 299.

As will be appreciated by a person of ordinary skill, an adaptor having features similar to adaptor 200 can be constructed to significantly increase the surface area of filter 190 without increasing the outside diameter of the adaptor by simply increasing the length of shaft 230 and increasing the length of filter 290. Elongating filter 290 and shaft 230 increases the surface area of filter 290 that is available for passage of the fluid without increasing the outer profile of the filter adaptor.

Figure 15:
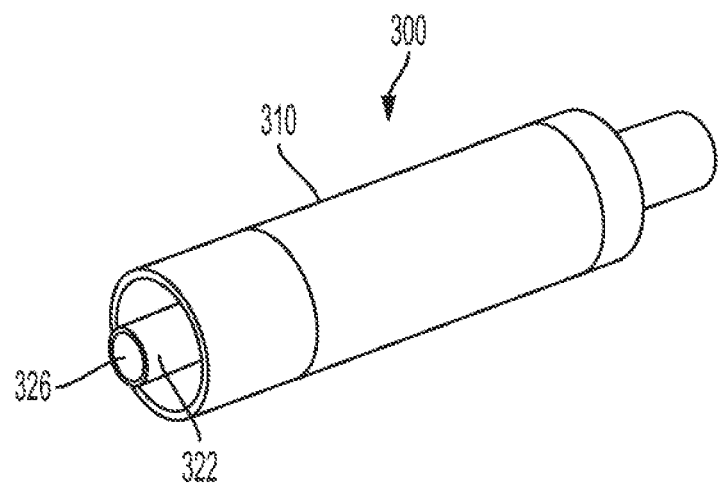
FIG. 15 is a perspective view of another filter adaptor embodiment according to the present disclosure.
Figure 16:
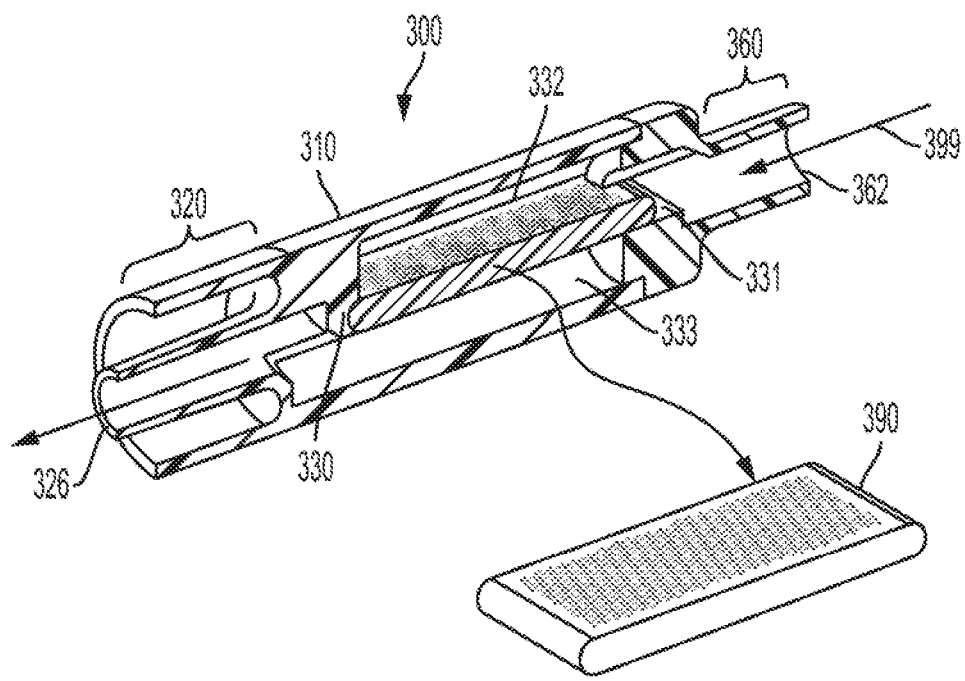
FIG. 16 is a cross-sectional view of the filter adaptor embodiment shown in FIG. 15 with an exploded view of the filter.

Another representative embodiment of a filter adaptor according to this aspect of the disclosure is depicted in FIGS. 15 and 16. Filter adaptor 300 differs from filter adapter 100 in that filter adaptor 300 does not include a cylindrical filter as used in filter adaptor 100. Rather filter adaptor 300 includes a generally planar filter block 390. Filter adaptor 300 includes main body 310 that includes connector 320 defining outlet port 326, connector 360 defining inlet port 362 and filter retaining brackets 330, 331 operable to retain planar filter block 390 is a longitudinal position separating first lateral passageway 332 from second lateral passageway 333. First lateral passageway 332 opens directly to inlet port 362. Second lateral passageway 331 opens directly to outlet port 326.

Connector 320 is configured as a luer connector and includes center mounting bore 322, which defines outlet port 326. Connector 360 defines inlet port 362 and is configured to connect with a tube. With reference to FIG. 16, arrows 399 show the fluid flow path into inlet port 362, through filter adaptor 300 and out through outlet port 326. More specifically, arrows 399 show directions of fluid flow in various areas of filter adaptor 300 from inlet port 362 through connector 360, and into first lateral passageway 332, where it is redirected through filter 390 into second lateral passageway 333, where it is again redirected toward outlet port 326.

In the embodiment shown, fluid flow is achieved in the direction of arrows 399 by application of a pressure gradient across filter adaptor 300 that is sufficient to pass the fluid through filter 390. Pressure may be applied by exerting a positive pressure on the inlet port side of filter adaptor 300 or by applying a negative pressure (i.e., suction) on the outlet port side of filter adaptor 300. Moreover, due to the construction of filter adaptor 300, it can be operated equally well with a fluid flow in the opposite direction of that described above, in which case outlet port 326 operates as an inlet port and inlet port 362 operates as an outlet port.

As will be appreciated by a person of ordinary skill, an adaptor having features similar to adaptor 300 can be constructed to significantly increase the surface area of filter 390 without increasing the outside diameter of the adaptor by simply increasing the length of adaptor 300 and increasing the length of filter 390. Elongating filter 390 increases the surface area of filter 390 that is available for passage of the fluid without increasing the outer profile of the filter adaptor.

In some embodiments, the main body and housing components of filter adaptors 100, 200 and 300 comprise polymeric material. Representative examples of polymers include, but are not limited to, polyurethanes, ionomers, polycarbonates, polysulphone, acrylic, polyamide, acrylonitrile-butadiene-styrene terpolymer, polyethylene terephthalate, polyoxymethylene, acrylonitrile, styrene acrylonitrile, styrene butadiene rubber, polyetheretherketone, or polyaryletherketone. In some embodiments, the filter adaptors comprise an acrylic polymer. In some embodiments, the filter adaptors comprise acrylonitrile-butadiene-styrene. In some embodiments, the filter adaptors comprise glass, fused silica, silicone, plastics (for example polytetraflouroethylene, polypropylene, polystyrene, polycarbonate, polymethylmethacrylate. and blends thereof), or metal. In some embodiments, the filter connector comprises polypropylene, polycarbonate, nylon, or PVDF material.

In some embodiments, the filter has a surface area of at least or about 10 square millimeters ($mm^2$), 40 $mm^2$, 90 $mm^2$, 150 $mm^2$, 245 $mm^2$, 350 $mm^2$, 480 $mm^2$, 625 $mm^2$, 790 $mm^2$, 980 $mm^2$ or 1960 $mm^2$. In some embodiments, the surface area of the filter is in a range of about 10 $mm^2$ to about 1960 $mm^2$, about 40 $mm^2$ to about 980 $mm^2$, or about 90 $mm^2$ to about 625 $mm^2$. In some embodiments, a filter adaptor has a length of at least or about 10 mm, 15 mm, 20 mm, 25 mm, 30 mm, 35 mm 40 mm, 45 mm or 50 mm. In some embodiments, the length of the filter adaptor is in a range of about 10 mm to about 50 mm, about 15 mm to about 40 mm, or about 20 mm to about 30 mm. In some embodiments, the outer diameter of the filter adaptor is at least or about 2 mm, 3 mm, 4 mm, 5 mm, 6 mm, 7 mm, 8 mm, 89 mm, or 10 mm. In some embodiments the outer diameter of the filter adaptor is in a range of about 3 mm to about 10 mm, about 4 mm to about 9 mm, or about 4 mm to about 8 mm. In some embodiments, an outer diameter of a filter is about 25 mm. In some embodiments, the filter adaptor has a ratio of filter surface area (in mm$^2$) to outer diameter (in mm) of at least or about 2:1, 5:1, 10:1, 15:1, 20:1, or 25:1. In some embodiments the ratio of surface area (in mm$^2$) to outer diameter (in mm) is in a range of about 2:1 to about 50:1, about 5:1 to about 25:1, or about 5:1 to about 20:1.

In another aspect of the disclosure, filter adaptors are provided that include a main body that define an internal fluid passageway, and a filter material comprising a gelling absorbent material contained within the passageway. The gelling absorbent material is capable, when in a dry state, of permitting passage of air, vapor and other gases therethrough upon application of a pressure gradient across the filter adaptor, and of absorbing aqueous fluid, such as exudate from a wound, when contacted thereby. Upon contact with the aqueous fluid, the gelling absorbent material converts to a gel and thereafter blocks passage of air, vapor and other gases through the main body of the filter adaptor. In various embodiments, the gelling absorbent material may be nonwoven, knitted or formed of a tight weave. The gelling absorbent material can expand upon absorption of aqueous fluid such as wound exudate or other fluid produced from a wound site. When the gelling absorbent material blocks passage of air, vapor and other gases through the main body of the filter adaptor, the blockage causes a pressure drop in the pump, which indicates that a dressing change is needed (i.e., wound exudate has reached the filter adaptor). In some embodiments, the gelling absorbent material also includes an indicator that functions as a blockage indicator or a dressing change indicator. In some embodiments, the indicator comprises symbols, letters, numbers, or color for indicating a change.

In some embodiments, the gelling absorbent material comprises a gel-forming fiber, filament, or agent. In some embodiments, the gel-forming fiber or filament is chemically-modified cellulose, alginate, or carboxymethyl cellulose, or a combination thereof. In some embodiments, the gel-forming fiber is carboxymethyl cellulose. The gelling absorbent material also can include other absorbent materials such as, for example, polyacrylate, polyacrylate fibers, bi-component superabsorbent fibers, air laid nonwovens, needlefelt nonwovens, thermobonded nonwovens and foams.

Some formulations of the gelling absorbent material contain an alginate to increase absorption capabilities. The active surface of the absorbent layer can be coated with a cross-linked adhesive mass containing a dispersion of gelatin, pectin and/or carboxymethyl cellulose together with other polymers. The polysaccharides and other polymers, when contacted with an aqueous fluid, absorb water and swell, forming a gel. The gel which is formed as a result of the absorption of water is held in place within the main body of the filter adaptor.

The gelling absorbent material preferably comprises gel forming fibres. The gel forming fibres can be of the type which retain their structural integrity on absorption of exudate or can be of the type which lose their fibrous form and become a structureless gel. The gel forming fibres are preferably spun sodium carboxymethylcellulose fibres, chemically modified cellulosic fibres, pectin fibres, alginate fibres, chitosan fibres, hyaluronic acid fibres, or other polysaccharide fibres or fibres derived from gums. The gel forming fibres are preferably sodium carboxymethylcellulose fibres, chemically modified cellulosic fibres, alkyl sulphonate modified cellulosic fibres such as those described in WO2012/061225, pectin fibres, alginate fibres, chitosan fibres, hyaluronic acid fibres, or other polysaccharide fibres or fibres derived from gums. The gel forming fibres are preferably chemically modified cellulosic fibres in the form of a fabric and in particular carboxymethylated cellulose fibres as described in PCT WO00/01425 to Azko Nobel UK Ltd. The cellulosic fibres preferably have a degree of substitution of at least 0.05 carboxymethyl groups per glucose unit. In another embodiment, the cellulosic fibres have a degree of substitution of from about 0.12 to about 0.35 as measured by IR spectroscopy (as defined in WO 00/01425). In another embodiment, the cellulosic fibres have a degree of substitution of from about 0.20 to about 0.30 and are made by carboxymethylating a woven or non-woven cellulosic fabric such that the absorbency is increased. The gel forming fibres preferably have an absorbency of at least 2 grams 0.9% saline solution per gram of fibre (as measured by the free swell method). Preferably the gel forming fibres have an absorbency of at least 10 g/g as measured in the free swell absorbency method, more preferably, between 15 g/g and 25 g/g.

The gelling absorbent material can be made in accordance with the disclosure of WO 93/12275, which describes the production of various absorbent carboxymethylated cellulosic products that are capable of absorbing many times their own weight of water.

Carboxymethylation can be achieved, for example, by sequential or simultaneous treatment of the cellulosic material with a strong alkali, such as aqueous sodium hydroxide, and monochloroacetic acid or a salt thereof. The appropriate reaction conditions will depend upon the composition of the fabric and the degree of carboxymethylation required and will be readily apparent to the person skilled in the art. They may be identical or similar to those described in WO 93/12275, WO 94/16746 or WO 00/01425. Desirably the carboxymethylation is carried out in the presence of industrial methylated spirits (IMS), and IMS is preferably also used in a subsequent washing step, suitably along with water, as a cleaner and steriliser.

In some embodiments, the gelling absorbent material comprises carboxymethylated cellulose fibres formed into a fabric. In other embodiments, the gelling absorbent material comprises two or more layers of fabric comprising carboxymethylated cellulose fibres. In some embodiments, the gelling absorbent material comprises compressed carboxymethylated cellulose. In some embodiments, the compressed carboxymethylated cellulose has a density of from about 10 to about 70 kg/cm$^3$. Various degrees of compression, and thus, various densities are envisioned and can be determined based upon the dimensions of a given filter adaptor and the fluid flow rate that is desired for the filter adaptor.

Figure 17:
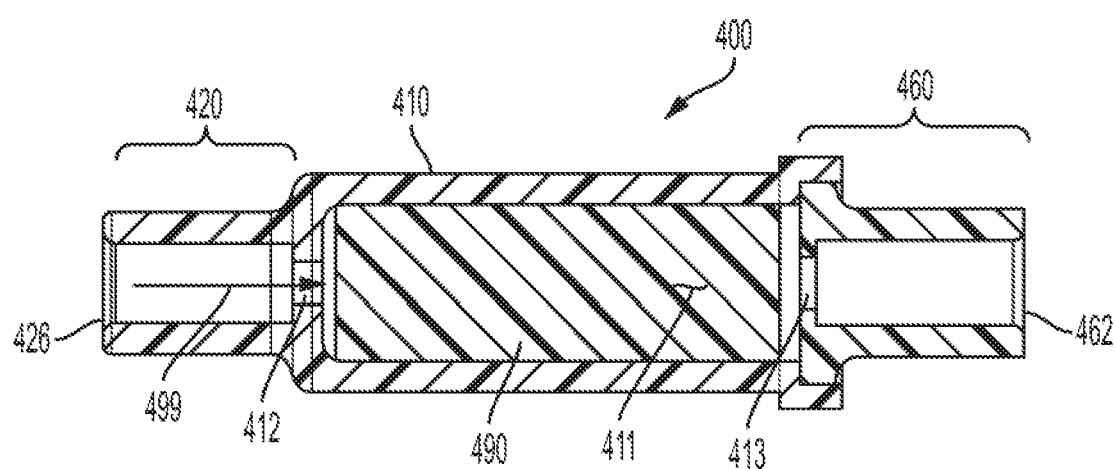
FIG. 17 is a schematic view of another filter adaptor embodiment according to the present disclosure.

With reference to the filter adaptor embodiment depicted in FIG. 17, filter adaptor 400 includes main body 410 that includes connector 420 defining inlet port 426, connector 460 defining outlet port 462 and defines a chamber 411 operable to retain filter 490 comprising gelling absorbent material. Main body 410 also defines apertures 412, 413 that fluidly connect chamber 411 to inlet port 426 and outlet port 462, respectively. Arrows 499 show the fluid flow path into inlet port 426, through filter adaptor 400 and out through outlet port 362. More specifically, arrows 499 show directions of fluid flow from inlet port 426 through connector 420, through aperture 412 and into chamber 411, where it passes through filter 490, then through aperture 413 into connector 460, and toward outlet port 462. In the embodiment shown, fluid flow is achieved in the direction of arrows 499 by application of a pressure gradient across filter adaptor 400 that is sufficient to pass the fluid through filter 490. Pressure may be applied by exerting a positive pressure on the inlet port side of filter adaptor 400 or by applying a negative pressure (i.e., suction) on the outlet port side of filter adaptor 400. Moreover, due to the construction of filter adaptor 400, it can be operated equally well with a fluid flow in the opposite direction of that described above, in which case outlet port 462 operates as an inlet port and inlet port 426 operates as an outlet port. As with other embodiments described herein, first connector 420 is configured for connection to a first conduit for fluid delivery into filter adaptor 400 and second connector 460 is configured for connection to a second conduit for fluid flow out of filter adaptor 400.

As will be appreciated by a person of ordinary skill, an adaptor having features similar to adaptor 400 can be constructed to significantly increase the volume of filter 490 without increasing the outside diameter of the adaptor by simply increasing the length of adaptor 400 and increasing the length of filter 490. Elongating filter 490 increases the volume of filter 490 that is available for passage of the fluid without increasing the outer profile of the filter adaptor.

In some embodiments, an outer dimension of filter adaptor 100, which is generally defined by the outer dimensions of hub 124 and outer side wall 180, filter adaptor 200, which is generally defined by the outer dimensions of seal 220, filter adaptor 300, which is generally defined by the outer dimensions of main body 310, and/or filter adaptor 400, which is generally defined by the outer dimensions of main body 410, is no more than 25 mm. In some embodiments, an outer dimension of the filter adaptor is at least or about 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 20 mm, 25 mm, or more than 25 mm. In some embodiments, an outer dimension of the filter adaptor is about 11 mm. In some embodiments, a length of the filter adaptor is no more than 30 mm. In some embodiments, a length of the filter adaptor is at least or about 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 20 mm, 25 mm, 30 mm, 35 mm, 40 mm, 45 mm, 50 mm, or more than 50 mm. In some embodiments, a length of the filter adaptor is about 25 mm.

Figure 18:
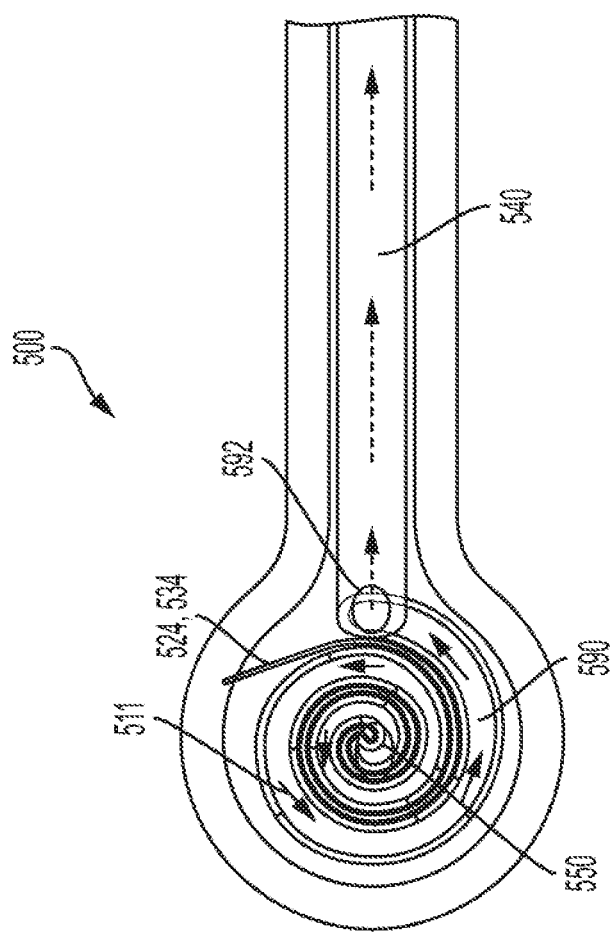
FIG. 18 is a top plan view of another filter adaptor embodiment according to the present disclosure.
Figure 19:
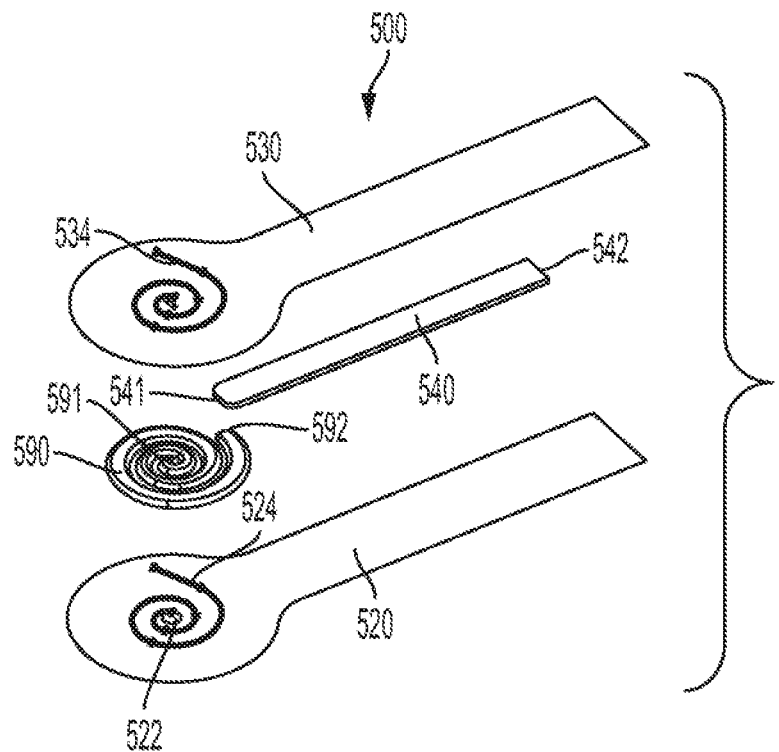
FIG. 19 is an exploded view of the filter adaptor embodiment shown in FIG. 18
Figure 20:
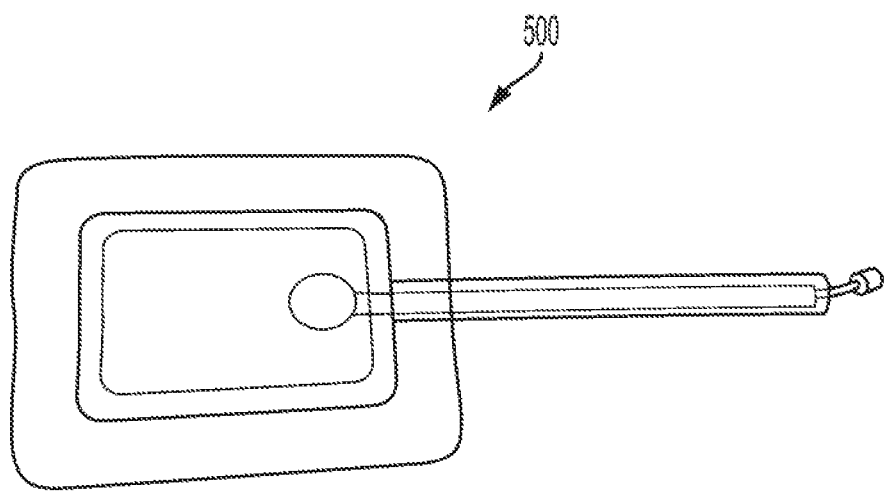
FIG. 20 shows the filter adaptor embodiment of FIG. 18 connected to a wound dressing.

Another filter adaptor embodiment that includes a filter composed of a gelling absorbent material is depicted in FIGS. 18-20. In filter adaptor 500, also referred to as spiral filter 500, chamber 511 that retains gelling absorbent material filter 590 is in the form of a spiral tube defining a spiral flow path. In alternate embodiments, chamber 511 can alternatively be formed into different shapes.

Filter adaptor 500 can be made, for example, by assembling four components as shown schematically in FIG. 19. Bottom layer 520 defines central aperture 522 and includes weld trace 524 to form chamber 511. Top layer 530 includes weld trace 534 having a shape and position that corresponds to weld trace 524 on bottom layer 520. Filter material 590 is shaped such that, when bottom layer 520, filter material 590 and top layer 530 are pressed together, first end 591 of filter material 590 lies adjacent central aperture 522 and filter material 590 extends in an outward spiral pattern between weld traces 524, 534 to a point where second end 592 of filter material 590 lies adjacent first end 541 of conduit 540. Filter material 590 can be formed into a desired shape, for example, by die punching the desired shape from a layer of the gelling absorbent material. When bottom layer 520, fiber material 590, conduit 540 and top layer 530 are positioned as described, weld traces 524, 534 are fused to one another by heat sealing or welding, such as, for example, radiofrequency welding or laser welding, to achieve filter adaptor 500 defining chamber 511 formed into spiral path with filter 590 contained therein. In one embodiment, filter adaptor 500 also includes indicator 550 situated adjacent central aperture 522 in the center of the spiral path. In some embodiments, the indicator is a blockage indicator or a dressing change indicator. In some embodiments, the indicator comprises symbols, letters, numbers, or color for indicating a change.

In some embodiments, filter adaptor 500 is mounted directly on a foam dressing or other negative pressure wound therapy dressing, such as that shown in FIG. 20. In this embodiment central aperture 522 is connected to an aperture or port in the cover layer of the dressing (not shown) that opens to the dressing/wound environment such that, upon connecting second end 542 of conduit 540 to a source of negative pressure, such as, for example, a vacuum pump (not shown), the negative pressure is transmitted through, conduit 540, through chamber 511 and central aperture 522 to the dressing/wound environment.

As will be appreciated by a person of ordinary skill, an adaptor having features similar to adaptor 500 can be constructed to significantly increase the volume of filter 590 without increasing the outside diameter of the adaptor by simply increasing the length of filter 590 and, if desired, increasing the number of spirals in filter adaptor 500. Elongating filter 590 increases the volume of filter 590 that is available for passage of the fluid without increasing the outer profile of the filter adaptor.

Filter Adaptor Uses

Filter adaptors as described herein may be used for various applications including negative pressure wound therapy, wound dressing, and syringe filters. In some embodiments, the filter adaptors are used for negative pressure wound therapy. For example, the filter adaptor is connected to a source of negative pressure, such as, for example, a vacuum pump for use in negative pressure wound therapy. In some embodiments, the filter adaptor comprises a tube connected to a dressing or, in some cases, such as, for example, a filter adaptor of the type shown in FIGS. 18-20, the filter adaptor can be connected directly to a dressing.

While a number of discrete embodiments have been described, aspects of each embodiment may not be specific to only that embodiment and it is specifically contemplated that features of embodiments may be combined with features of other embodiments. As will be appreciated from the descriptions herein and the associated Figures, a wide variety of aspects and embodiments are contemplated by the present disclosure, examples of which include, without limitation, the aspects and embodiments listed below: A filter adaptor that includes (i) a body that defines an internal passageway disposed between an inlet and an outlet, the passageway configured to permit passage of a fluid in a first direction defined by the inlet and the outlet; and (ii) a filter disposed within the passageway and oriented to define a volumetric direction that is different than the first direction.

A filter adaptor in accordance with any other embodiment disclosed herein, wherein the volumetric direction is perpendicular to the first direction.

A filter adaptor in accordance with any other embodiment disclosed herein, wherein the volumetric direction and the first direction are offset by an angle of at least 15°.

A filter adaptor in accordance with any other embodiment disclosed herein, wherein the filter adaptor has a tubular shape and has an outside diameter, and wherein the filter has a surface area that is independent of the outside diameter.

A filter adaptor in accordance with any other embodiment disclosed herein, wherein the outside diameter is from about 3 mm to about 15 mm.

A filter adaptor in accordance with any other embodiment disclosed herein, wherein the filter is cylindrical.

A filter adaptor in accordance with any other embodiment disclosed herein, wherein the filter is planar.

A filter adaptor in accordance with any other embodiment disclosed herein, wherein the filter lies on a plane that is not perpendicular to the first direction.

A filter adaptor in accordance with any other embodiment disclosed herein, wherein the filter lies on a plane that forms an angle with the first direction, and wherein the angle is less than 45°.

A filter adaptor in accordance with any other embodiment disclosed herein, wherein the body includes a first connector at the inlet and a second connector at the outlet.

A filter adaptor in accordance with any other embodiment disclosed herein, wherein each of the first connector and the second connector comprises a barb, hose, or luer connector.

A filter adaptor in accordance with any other embodiment disclosed herein, further comprising an indicator positioned within the internal passageway.

A filter adaptor in accordance with any other embodiment disclosed herein, wherein the indicator detects blockage or detects a need for a dressing change.

A filter adaptor in accordance with any other embodiment disclosed herein, wherein the indicator sensor comprises symbols, letters, numbers, or a color change.

A filter adaptor in accordance with any other embodiment disclosed herein, wherein the filter comprises gas permeable material.

A filter adaptor in accordance with any other embodiment disclosed herein, wherein the filter comprises liquid impermeable material.

A filter adaptor in accordance with any other embodiment disclosed herein, wherein the filter is gas permeable and liquid impermeable.

A filter adaptor in accordance with any other embodiment disclosed herein, wherein the filter is hydrophobic.

A filter adaptor that includes (i) a body that defines an internal passageway disposed between an inlet and an outlet, and (ii) a filter disposed within the passageway, wherein the filter comprises a gelling absorbent material that, when in a dry state, is permeable to gas and that, when contacted by an aqueous fluid, converts to a gel.

A filter adaptor in accordance with any other embodiment disclosed herein, wherein the gelling absorbent material comprises a gel-forming fiber.

A filter adaptor in accordance with any other embodiment disclosed herein, wherein the gelling absorbent material comprises a compressed gel-forming fiber.

A filter adaptor in accordance with any other embodiment disclosed herein, wherein the compressed gel-forming fiber has a density of from about 10 to about 70 kg/cm$^3$.

A filter adaptor in accordance with any other embodiment disclosed herein, wherein the internal passageway comprises a spiral path.

While embodiments of the present disclosure have been shown and described herein, it is to be understood by those skilled in the art that such embodiments are provided by way of example only. Numerous variations, changes, and substitutions will now occur to those skilled in the art without departing from the disclosure. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A filter adaptor, comprising:
   a body that defines an internal passageway disposed between an inlet and an outlet, the passageway configured to permit passage of a fluid in a first direction defined by the inlet and the outlet;
   a filter disposed within the passageway and oriented to define a volumetric direction that is different than the first direction; and
   an indicator positioned within the internal passageway;
   wherein the indicator detects blockage or detects a need for a dressing change
   wherein the body comprises a first component comprising the inlet, and a second component comprising the outlet; and
   wherein the first component and the second component are releasably coupled to one another.

2. The filter adaptor of claim 1, wherein the volumetric direction is perpendicular to the first direction.

3. The filter adaptor of claim 1, wherein the volumetric direction and the first direction are offset by an angle of at least 15°.

4. The filter adaptor of claim 1, wherein the filter adaptor has a tubular shape and has an outside diameter, and wherein the filter has a surface area that is independent of the outside diameter.

5. The filter adaptor of claim 4, wherein the outside diameter is from about 3 mm to about 15 mm.

6. The filter adaptor of claim 1, wherein the filter is cylindrical.

7. The filter adaptor of claim 1, wherein the body includes a first connector at the inlet and a second connector at the outlet.

8. The filter adaptor of claim 1, wherein the indicator comprises symbols, letters, numbers, or a color change.

9. The filter adaptor of claim 1, wherein the filter comprises gas permeable material.

10. The filter adaptor of claim 1, wherein the filter comprises liquid impermeable material.

11. The filter adaptor of claim 1, wherein the filter is gas permeable and liquid impermeable.

12. The filter adaptor of claim 1, wherein the filter is hydrophobic.

13. The filter adaptor of claim 1, wherein the filter is planar.

14. The filter adaptor of claim 13, wherein the filter lies on a plane that is not perpendicular to the first direction.

15. The filter adaptor of claim 13, wherein the filter lies on a plane that forms an angle with the first direction, and wherein the angle is less than 45°.

\* \* \* \* \*